(12) United States Patent
Han et al.

(10) Patent No.: US 6,514,689 B2
(45) Date of Patent: *Feb. 4, 2003

(54) HYDROGEL BIOSENSOR

(75) Inventors: In Suk Han, Sandy, UT (US); Jules John Magda, Salt Lake City, UT (US); Seok Lew Lew, Salt Lake City, UT (US); Young San Jean, Seoul (KR)

(73) Assignee: M-Biotech, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/839,993

(22) Filed: Apr. 20, 2001

(65) Prior Publication Data

US 2002/0042065 A1 Apr. 11, 2002

Related U.S. Application Data

(63) Continuation-in-part of application No. 09/644,323, filed on Aug. 23, 2000, which is a continuation-in-part of application No. 09/308,392, filed on May 11, 1999, now Pat. No. 6,268,161.
(60) Provisional application No. 60/199,057, filed on Apr. 22, 2000.

(51) Int. Cl.$^7$ .............................. C12Q 1/00; C12M 1/34; A61K 9/22
(52) U.S. Cl. ..................... 435/4; 435/287.1; 435/287.7; 604/891.1; 604/892.1
(58) Field of Search ................................. 435/4, 14, 25, 435/287.1, 287.7; 436/95, 148; 604/891.1, 892.1

(56) References Cited

U.S. PATENT DOCUMENTS 3,869,676 A 3/1975 Harrison et al. ............ 329/204
4,703,756 A 11/1987 Gough et al. ............... 123/635

(List continued on next page.)

2001/0016683 A1 8/2001 Darrow et al.

OTHER PUBLICATIONS

Miyata, T., Jikihara, A., Nakame, K. "Preparation of poly-(glucosyloxyethyl methacrylate)–Concanavalin A Complex Hydrogel and It's Glucose–Sensitivity," Macrol. Chem. Phys., 1996, pp. 1135–1146, vol. 197.

(List continued on next page.)

*Primary Examiner*—David A. Redding

(57) ABSTRACT

A biosensor (10) has a hydrogel (30) in a rigid and preferably biocompatible enclosure (20). The hydrogel (30) includes an immobilized analyte binding molecule (ABM) and an immobilized analyte. The immobilized analyte competitively binds with free analyte to the ABM, thus changing the number of crosslinks in the hydrogel (30), which changes hydrogel swelling tendency (and thus the osmotic pressure) in its confined space in proportion to the concentration of free analyte concentration. By measuring the change in hydrogel pressure with a pressure transducer (40), the biosensor (10) is able to accurately measure the concentration of the free analyte molecule without the problem of oxygen limitations and interference encountered by prior art biosensors. A battery (64) powered telemeter (60) operably engaged to the pressure transducer (40) sends a radio data signal to a receiver (66) containing an alarm system operably attached to a computer (62). Furthermore, an alarm system utilizes such a sensor to automatically notify a person that the analyte level is outside desired predetermined parameters, and/or to automatically inject an agent to counteract the adverse analyte levels.

27 Claims, 23 Drawing Sheets

U.S. PATENT DOCUMENTS

| | | | |
|---|---|---|---|
| 4,919,141 A | 4/1990 | Zier et al. | 128/635 |
| 5,141,873 A | 8/1992 | Steudle et al. | |
| 5,305,745 A | 4/1994 | Zacouto | |
| 5,372,133 A | 12/1994 | Esch | 128/631 |
| 5,431,160 A | 7/1995 | Wilkins | 128/635 |
| 5,593,852 A | 1/1997 | Heller et al. | 435/143 |
| 5,665,065 A | 9/1997 | Coleman et al. | 604/66 |
| 5,711,291 A | 1/1998 | Takaki | 128/667 |
| 5,752,918 A | 5/1998 | Fowler et al. | 600/488 |
| 5,967,975 A | 10/1999 | Ridgeway | 600/300 |
| 5,995,860 A | 11/1999 | Sun et al. | 600/341 |
| 6,102,856 A | 8/2000 | Groff et al. | 600/301 |
| 6,113,539 A | 9/2000 | Ridenour | 600/300 |
| 6,150,942 A | 11/2000 | O'Brien | 340/573.1 |
| 6,198,394 B1 | 3/2001 | Jacobsen et al. | 340/573.1 |
| 6,268,161 B1 * | 7/2001 | Han et al. | 435/14 |

OTHER PUBLICATIONS

Kivalo.com website. Smith, Richard W., President, "KIVALO and Stonestreet One Working on Bluetooth Wireless Medical Monitors," www.kivalo.com/news_01_03_06.html (North Carolina).

Baek, Seong–Gi, "Novel Rheological Techniques Applied to Investigate Rheology of Liquid Crystal Polymers," Dept. of Chem. Eng., 1991, Univ. of Utah, pp. 1–218.

Brondsted, H., *Polyelecrolyte Gels: Properties Preparation, and Application*, 1992, pp. 295–302, Washington, D.C.

Foulds, N.C., Frew, J.E., and Green, M.J., "Immunoelectrodes," *Biosensors: a Practical Approach*, 1990, pp. 97–125, IRL Press, Oxford University.

Fryer, T., "A Pressure Telemetry System Utilizing a Capacitance–Type Transducer," *Biotelemetry III*, 1976, pp. 279–282, Academic Press, New York.

Ghandehari, H., et al., "Biodegradable and pH Sensitive Hydrogels: Synthesis by a Polymer–Polymer Reaction," J. Macrol. Chem. Phys., 1996, pp. 965–980, vol. 197.

Harrison, D.R., and Dimeff, J., "A Diode–Quad Bridge Circuit for Use With Capacitance Transducers," Rev. Sci. Instrum., 1973, pp. 1468–1472, vol. 44.

Ito, Y., et al., "An Insulin–Releasing System That Is Responsive to Glucose," J. Controlled Release, 1989, pp. 195–203, vol. 10.

Ishihara, K., et al., "Glucose Induced Permeation Control of Insulin Through a Complex Membrane Consisting of Immobilized Glucose Oxidase and a Poly(amine)," Polym. J., 1984, pp. 625–631, vol. 16.

Kim, S.W., et al., "Hydrogels: Swelling, Drug Loading, and Release," Pharm. Res., 1992, pp. 283–290, vol. 9.

Kost, J., et al., "Glucose–Sensitive Membranes Containing Glucose Oxidase: Activity, Swelling and Permeability Studies," Biomed. Mater Res., 1985, pp. 1117–1133, vol. 19.

Lee, Chang–Soon, Magda, J.J., De Vries, K.L., and Mays, J.W., "Measurements of the Second Normal Stress Difference for Star Polymers with Highly Entangled Branches," Macromolecules, 1992, pp. 4744–4750, vol. 25.

Lee, Chang–Soon, Tripp, B.C., and Magda, J.J., "Does $N_1$ or $N_2$ Control the Onset of Edge Fracture?" Rheologica Acta, 1992, pp. 306–308, vol. 31.

Magda, J.J., Lou, J., Baek, S.G., and De Vries, K.L., "Second Normal Stress Difference of a Boger Fluid," Polymer, 1991, pp. 2000–2009, vol. 32.

Magda, J.J., Baek, S.G., De Vries, K.L., and Larson, R.G., "Unusual Pressure Profiles and Fluctuations During Shear Flows of Liquid Crystal Polymers," Polymer, 1991, pp. 1794–1797, vol. 32.

Magda, J.J., Baek, S.G., De Vries, K.L., and Larson, R.G., "Shear Flows of Liquid Crystal Polymers: Measurements of the Second Normal Stress Difference and the Doi Molecular Theory," Macromolecules, 1991, pp. 4460–4468, vol. 24.

Obaidat, a., and Park, K., "Characterization of Protein Release Through Glucose–Sensitive Hydrogel Membranes," Biomaterials, 1997, pp. 801–806, vol. 18.

Sato, S., et al., "Self–Regulating Insulin Delivery Systems," J. Controlled Release, 1984, pp. 67–77, vol. 1.

Schott, H., "Kinetics of Swelling of Polymers and Their Gels," J. Pharm. Sci., 1992, pp. 467–470, vol. 81.

Serres, Anne, et al., "Temperature and pH–sensitive Polymers for Human Calcitonin Delivery," Pharm. Res., 1996, pp. 196–201, vol. 13.

Tandeske, Duane, Chapter 5: *Pressure Sensors: Selection and Application*, 1991, New York, pp. 77–115.

Updike, S.J., et al., "Enzymatic Glucose Sensors: Improved Long Term Performance In Vitro and In Vio," ASAIO Journal, 1994, pp. 157–163, vol. 40.

Wilkins, E.S., "Towards Implantable Glucose Sensors: A Review," J. Biomed. Eng., 1989, pp. 354–361, vol. 11.

Yoshitake, S., Imagawa, M., and Ishikawa, E., "Efficient Preparation of Rabbit Fab'–Horseradish Peroxidase Conjugates Using Malemide Compound and Its Use for Enzyme Immunoassay," Anal. Lett., 1982, pp. 147–160, vol. 15.

Yoshitake, S., Imagawa, M., Ishikawa, E., Niitsu, Y., Urushizaki, I., Nishiura, M., Kanazawa, R., Kurosaki, H., Tachibana, S., Nakazawa, N., and Ogawa, H., "Mild and Efficient Conjugation of Rabbit Fab' and Horseradish Perosidase Using a Maleimide Compound and Its Use for Enzyme Immunoassay," Biochem., 1982, pp. 1413–1424, vol. 92.

* cited by examiner

HYDROGEL BIOSENSOR

RELATED APPLICATIONS

The present application is a continuation-in part of U.S. Patent Application Ser. No. 09/644,323, which was filed on Aug. 23, 2000, which is a continuation-in-part of U.S. Patent Application Ser. No. 09/308,392, filed on May 11, 1999, now U.S. Pat. No. 6,268,161 and claims the benefit of Provisional Patent Application Ser. No. 60/199,057 which was filed on Apr. 22, 2000.

STATEMENT OF GOVERNMENT INTEREST

This invention was made with government support under R43DK55958 (grant no.) awarded by National Institute of Health. The Government has certain rights in the invention.

BACKGROUND OF THE INVENTION

1. Field of the Invention

This invention relates generally to biosensors utilizing hydrogels to measure the concentration of free analyte molecules in a fluid, particularly biosensors suitable for implantation in a patient to provide constant monitoring of a selected analyte. The invention also relates to health alarm systems in which a biosensor is connected to apparatus which alerts a patient and/or patient caretakers to deleterious changes in the levels of analyte in the patient's body fluids or to other adverse changes in a patient's condition.

2. Description of Related Art

During the past decade, intense effort has been directed toward the development of analyte monitoring biosensors as an aid to prevent complications of diseases such as diabetes. Development of an implantable analyte sensor that is specific and sensitive enough to precisely and continuously monitor analyte levels in vivo would be a significant advance. Such a sensor would also greatly facilitate data collection and biochemical research relating to analyte levels in patients.

Several new implantable techniques have been developed for analyte analysis such as glucose in clinical practice based on electrochemical principles and employing enzymes such as glucose oxidase (GOD) for analyte recognition. Potentially implantable analyte biosensors based on electrochemical transducers are the most highly developed, and this class of sensors can be further subdivided into potentiometric sensors, conductometric sensors, and amperometric sensors. At present, neither the potentiometric method nor the conductometric method appears to be suitable for in vivo analyte monitoring due to: (a) interference by species other than analyte in the physiological environment; (b) low sensitivity and logarithmic dependence of the signal on the analyte concentration. A linear dependence of the signal on analyte concentration is highly desirable because of the need for repeated recalibrations over time for implanted analyte sensors. However, non-linear calibration curves can be handled reasonably well using microprocessors.

The most advanced analyte sensors for in vivo monitoring are electrochemical sensors containing hydrogels in which an enzyme which generates hydrogen peroxide upon reaction with the analyte is immobilized, with an amperometric method being used to detect the hydrogen peroxide. This technique offers the possibility for a linear calibration curve. In the amperometric method, an electrode is used which produces a current proportional to the diffusional flux of hydrogen peroxide ($H_2O_2$) to the electrode surface, or, alternatively, proportional to the diffusional flux of oxygen ($O_2$) to the electrode surface. An increase in the surrounding analyte concentration should increase the diffusional flux of analyte into the membrane and increase the reaction rate within the membrane. The increase in enzymatic reaction rate in turn should increase the local hydrogen peroxide concentration and decrease the local oxygen concentration within the membrane. This should lead to an increase in the current detected by a hydrogen peroxide-based electrode sensor, or a decrease in current as detected by an oxygen-based electrode sensor. The latter approach, based on detecting the oxygen flux, also requires a second oxygen-based electrode sensor located in a hydrogel without the enzyme. This second electrode is used as a reference.

However, amperometric sensors must overcome several hurdles before they will ever be useful for commercial in vivo monitoring. Current analyte sensor designs appear unlikely to solve these difficult problems in the near future. The first hurdle arises from electrochemical interference. The analyte (whether hydrogen peroxide or oxygen) must be the only species present which produces a current at the electrode. Hence for both oxygen-based and hydrogen peroxide-based analyte sensors, an inner membrane must be used which is permeable to the analyte but impermeable to endogenous interferents which may produce electrochemical effects. In clinical studies of the hydrogen peroxide-based sensor, a decay in sensitivity over the implant period was observed, a phenomenon which could not be explained by blockage of the sensor surface by protein. One possible explanation for the loss of sensitivity is hydrogen peroxide mediated enzyme deactivation. For the oxygen-based sensor, this can be avoided by co-immobilizing catalase with enzyme, because catalase consumes hydrogen peroxide. Fourthly, a shortage of oxygen relative to analyte can place an upper limit on the biosensor's ability to measure analyte levels. This problem is called the "oxygen deficit".

In addition to the biosensors described above, hydrogels have also been used in devices developed to release insulin directly into a diabetic's bloodstream in response to high analyte levels. In one approach, the hydrogel is constructed to have chemically immobilized pendant groups which are charged under physiological conditions (pH2 to pH10). Molecules of glucose and of a glucose-specific binding molecule (abbr. GBM; for example, concanavalin A) are also immobilized in the gel. Within the hydrogel, in a solution which contains no free glucose, immobilized glucose molecules bind to immobilized GBMs, forming what are in effect non-covalent 'crosslinks'. As the hydrogel is exposed to a fluid containing free glucose, binding competition displaces immobilized glucose from GBMs, thus reducing the number of 'crosslinks'. This reduction in crosslinking causes an increase in swelling of the hydrogel, due to the presence of the charged pendant moieties in the hydrogel. In effect, the hydrogel swelling increases the porosity and/or pore size between gel subunits. These insulin-delivery hydrogels also contain insulin, and the increase in pore size in turn allows insulin (a rather large molecule which does not diffuse readily through a closely-crosslinked gel matrix) to diffuse outward and be released into the patient's bloodstream. See A. Obaidat, et al., Characterization of Protein Release through Glucose-sensitive Hydrogel Membranes, 18 BIOMATERIALS 801–806 (1997); Y. Ito, et al., An Insulin-releasing System that is Responsive to Glucose, 10 JOURNAL OF CONTROLLED RELEASE 195–203 (1989), which are expressly incorporated herein.

However, so far as we are aware, the changes in swelling force/osmotic pressure that occur in pH-sensitive competition binding hydrogels have not heretofore been recognized and exploited for the measurement of the concentration of free analyte. The prior art does not teach measurement of the analyte-induced swelling of the hydrogel as a method of measuring analyte concentrations, and it specifically does not teach the use of a transducer to measure hydrogel swelling. The use of a pressure transducer provides a measurement tool that avoids the problems encountered by electrochemical sensors.

Thus, a need exists for a biosensor that is extremely sensitive to the concentration of analyte, and also relatively free from interference, even when operating in complex media such as human blood. A need further exists for a biosensor that relies directly on change in analyte, since analyte concentration itself is a much more controlled parameter than parameters measured by electrodes. This is especially critical in implantable biosensors, because this system is relatively free from potential sources of interference. Additionally, there is a need for hydrogel-based biosensors in which the analyte-detecting process does not consume oxygen.

Accordingly, it is the object of this invention to provide such a biosensor. It is a further object to provide a general method for measuring the concentration of any analyte for which a suitable specific binding partner can be found or constructed.

SUMMARY OF THE INVENTION

The present invention comprises a hydrogel-based biosensor which measures the osmotic pressure within a hydrogel having pendant charged moieties, analyte molecules, and analyte binding partner molecules all immobilized within. In order to measure the osmotic pressure or swelling tendency of the hydrogel, the gel is confined in a rigid enclosure that has a semipermeable opening to permit osmotic contact between the test fluid (a patient's blood or other solution) and pressure detection means are operably associated with the hydrogel for detecting the osmotic pressure or swelling tendency of the hydrogel. The device uses a competition assay, in which free analyte molecules diffusing into the hydrogel displace immobilized analyte molecules in proportion to the free analyte concentration. This displacement reduces the degree of 'crosslinking' between immobilized analyte and immobilized analyte binding partner molecules, and, since the hydrogel also contains pendant charged moieties, reduction in 'crosslinking' results in a change in swelling propensity, or osmotic pressure, detectable by the pressure detection means.

Thus, a biosensor of the invention comprises a polymeric hydrogel having pendant moieties that are charged under physiological conditions, an analyte binding molecule immobilized in the hydrogel and capable of binding the free analyte, analyte molecules immobilized in the hydrogel, and pressure detection means for measuring the osmotic pressure of the hydrogel. In the preferred embodiment, the pressure detection means is comprised of a diaphragm positioned such that changes in osmotic pressure within the gel cause changes in pressure exerted on the diaphragm, and a pressure transducer operably associated with the diaphragm for detecting these pressure changes. Biosensors of this invention can be designed to detect any analyte which can be immobilized within the hydrogel and for which an (immobilizable) binding partner with sufficient specificity and binding affinity can be found (see Table 1).

To derive analyte concentration readings, it is necessary to calibrate the detected pressure changes against solutions of known analyte concentration, as is commonly done for other measuring techniques. Accordingly, a further embodiment of the biosensor includes reporting means associated with the pressure detection means for reporting the data signal, and computing means operably disposed to receive the data signal and constructed to compare it to a predetermined calibration curve and to produce an analyte data signal reflecting the measured analyte concentration.

In a preferred embodiment, the reporting means is a battery powered telemeter which sends a radio data signal to a receiver operably attached to the computing means. In a further preferred embodiment, the computing means is associated with an alarm system. The computing means may be a personal computer, but in a preferred embodiment, the computing means is a microprocessor.

In a more highly preferred embodiment, the computing means contains or is operably associated with alarm means for providing an alarm signal when the analyte concentration falls outside a pre-determined acceptable range. In a further highly preferred embodiment, the biosensor unit carried in or on the patient's body includes a GPS (global positioning system) unit.

Thus, a further invention described herein comprises biosensor-based health alarm system which provides a warning of an adverse condition detected by a biosensor to care providers at a location remote to the patient via telephone or wireless transmission means. In a highly preferred embodiment, the system includes a GPS unit and a wireless phone, thus providing monitoring and alarm coverage to the patient while travelling. The biosensor of the system may be any sensor configured to detect a critical health-related biological determinant (such as, but not limited to, the concentration of a selected analyte in the patient's body fluid). The system may further include an automatic drug administration component which responds to the sensor by administering an appropriate amount of a drug to ameliorate the adverse effects of the change in the biological determinant.

The invention also encompasses a method of determining the concentration of free analyte in a solution. The method comprises steps of: providing a hydrogel having pendant charged moieties, analyte molecules, and analyte-specific binding molecules covalently immobilized therein; enclosing the hydrogel in a rigid structure which has at least one permeable portion available for contacting a test fluid with the hydrogel, the permeable portion constructed to permit free analyte to diffuse into the hydrogel; contacting the hydrogel sequentially with a series of calibration solutions having known concentrations of free analyte and measuring osmotic pressure in the hydrogel for each of the calibration solutions to produce a calibration curve of osmotic pressure versus analyte concentration; contacting the hydrogel with the test fluid, and measuring a resulting osmotic pressure; and comparing the resulting osmotic pressure with the calibration curve to determine analyte concentration of the test fluid.

The steps involving measuring the osmotic pressure are preferably accomplished by disposing pressure sensing means within the rigid structure and in contact with the hydrogel, the pressure sensing means producing a data signal reflective of the osmotic pressure.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
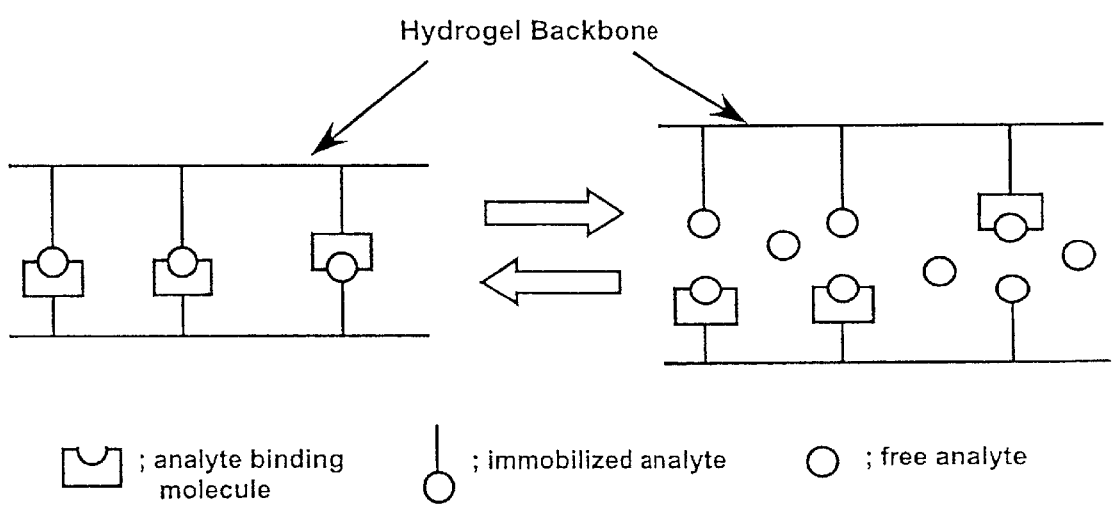
FIG. 1 is an example of the competitive binding and swelling mechanism.
Figure 2:
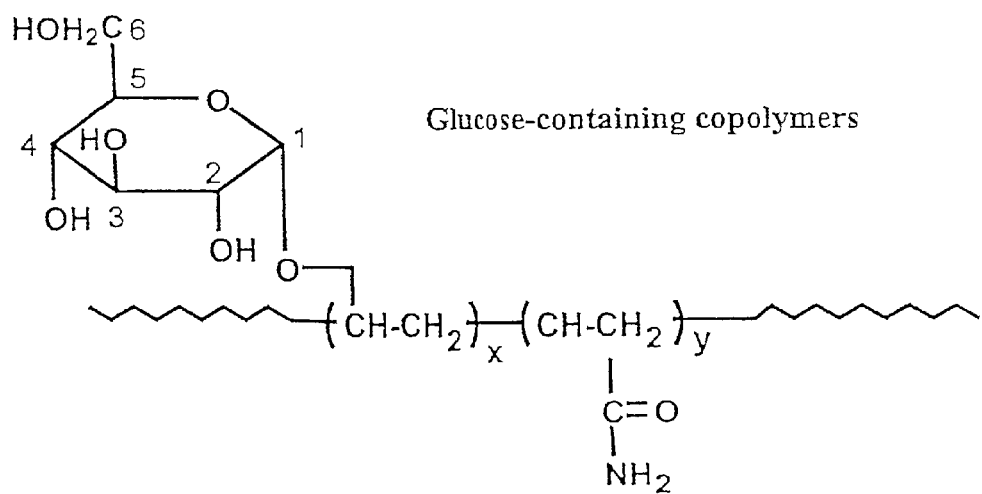
FIG. 2 is an example of an analyte binding molecule (ABM)-containing copolymer.

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the claims.

The above-described drawing figures illustrate the invention, a biosensor 10 for measuring the concentration of analyte in a solution. In its broadest description, the biosensor 10 uses a special polymeric hydrogel 30 that changes its osmotic pressure in proportion to the concentration of free analyte; ABM immobilized in the hydrogel 30, the ABM competitively binds with immobilized analyte and free analyte, thereby causing the hydrogel 30 to change its osmotic pressure; a means for measuring 40 the osmotic pressure of the hydrogel 30; and a means for reporting 60 the concentration of analyte based on the measured osmotic pressure of the hydrogel 30. In its preferred embodiment, the biosensor 10 includes a rigid, biocompatible enclosure 20 having semipermeable membrane 26 covering an open end 22, a flexible diaphragm 28 between the semipermeable membrane 26 and the closed end 24, and a polymeric hydrogel 30 enclosed therebetween, the hydrogel 30 including moieties that cause the hydrogel 30 to change its osmotic pressure in proportion to the free analyte of the hydrogel 30.

The enclosure 20 is designed to be dipped into a sample and implanted directly into the human body for monitoring blood analyte levels. In this embodiment, the biosensor 10 uses ABM immobilized in a hydrogel 30. The means for measuring 40 the osmotic pressure of the hydrogel 30 is preferably a pressure transducer 40 operably associated with the flexible diaphragm 28. The means for reporting 60 analyte levels is preferably a battery 64 operated telemeter 60 that sends a radio data signal to a receiver operably attached to a computer 62. Alternative embodiments of this biosensor 10 can easily be adapted by those skilled in the art. Rather than use of a telemeter 60, a direct electrical connection to a computer 62 can be used when the biosensor 10 is minimally invasive into a human body. While the pressure transducer 40 is currently the preferred tool for measuring changes in the osmotic pressure of the hydrogel 30, those skilled in the art can devise alternative means of measuring and reporting changes in the osmotic pressure of the hydrogel 30. One alternative method is to use a piezoelectric and a piezoresistive sensor on place of the pressure transducer 40.

The Enclosure, Semipermeable Membrane, and Diaphragm

Figure 3:
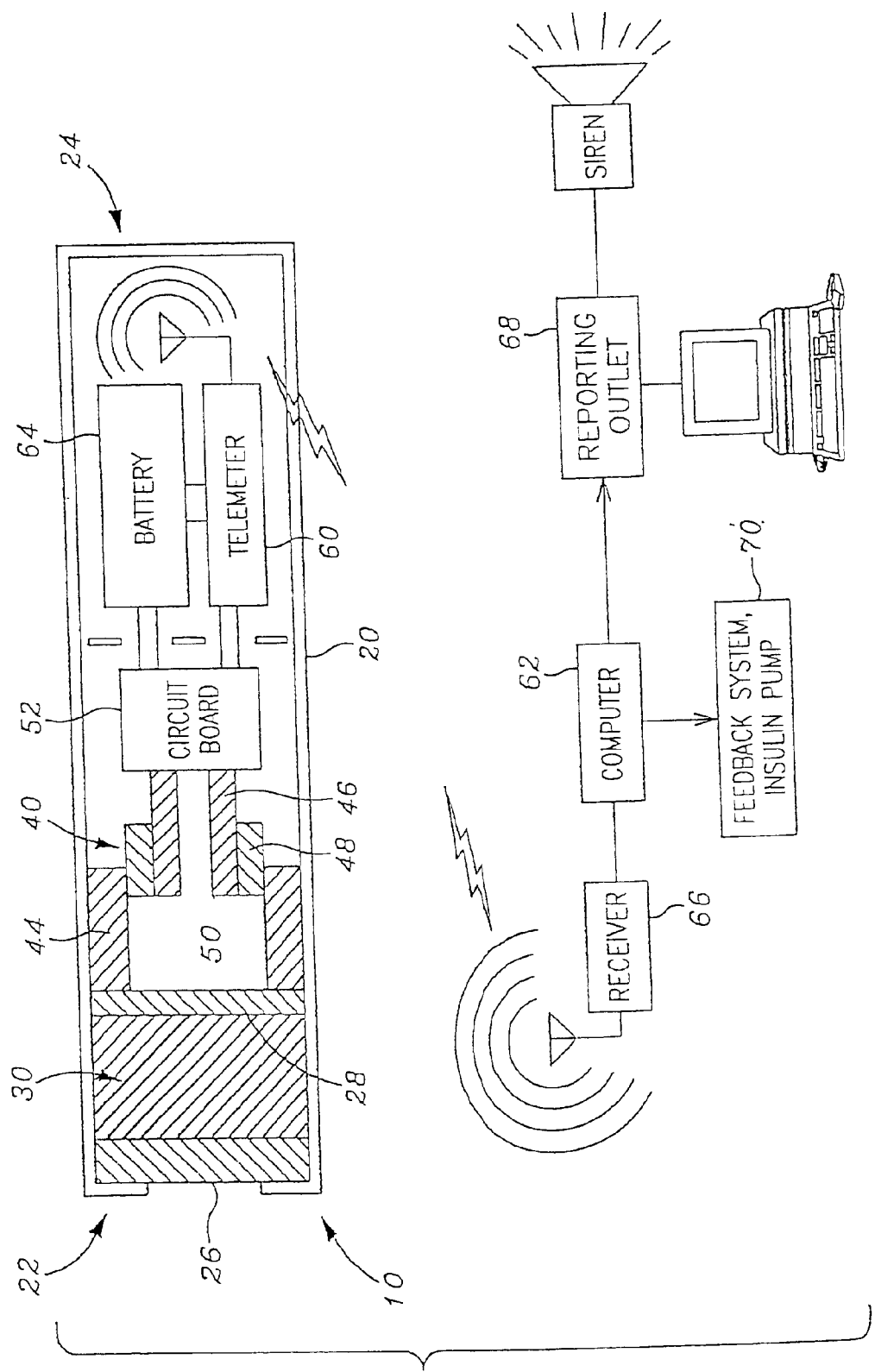
FIG. 3 is a side, partial cross-sectional view and diagram of the preferred embodiment of the present invention, showing a biosensor that can be dipped in a sample and implanted under a patient's skin.

As best seen in FIG. 3, the structure of the biosensor 10 is provided by an enclosure 20, preferably a cylindrical enclosure 20 having an open end and a closed end. The open end is sealed with a semipermeable membrane 26. A flexible diaphragm 28 is mounted between the semipermeable membrane 26 and the closed end. The hydrogel 30, described below, is enclosed between the semipermeable membrane 26 and the diaphragm 28. The enclosure 20 is preferably constructed of a rigid, impermeable, and biocompatible material such as stainless steel; and the enclosure 20 is preferably conjugated with heparin to prevent blood clotting, and polyethylene glycol (PEG) to decrease the body's immune response against the enclosure 20. The enclosure 20 is preferably coating with a biocompatable material such as a thin polymer. The enclosure 20 is preferably cylindrical in shape to facilitate implantation, the cylinder being approximately 5 to 12 mm long and having a diameter of approximately 0.1 to 3 mm. If the enclosure 20 will not be implanted, any rigid and impermeable material such as fiber, plastic or metal can be used.

The semipermeable membrane 26 is permeable to the passage of small analytes; however, it is impermeable to the passage of blood clots, cells, proteins, and the hydrogel 30. The semipermeable membrane 26 is preferably made of a material rigid enough to sustain the pressure of a swollen analyte sensitive hydrogel 30. If the biosensor 10 is to be implanted into the human body, the semipermeable membrane 26 is preferably an inert, nontoxic material. A suitable semipermeable material can be selected from, but is not limited to, the following groups of polymers: cellulose acetate, methyl cellulose, polyvinyl alcohol, and polyurethane. The semipermeable materials are also preferably conjugated with heparin and polyethlyene glycol (PEG) to decrease immunogenic response, blood clotting and cell attachment on the surface. Examples of such enclosures and semipermeable membranes are discussed in Heller, U.S. Pat. No. 5,593,852, Wilkins, U.S. Pat. No. 5,431,160, Hogen Esch, U.S. Pat. No. 5,372,133, Zier, U.S. Pat. No. 4,919,141, and Gough, U.S. Pat. No. 4,703,756, all hereby incorporated in full by reference.

The diaphragm 28 is preferably be a flexible but conductive material useful for use with a transducer 40. Such diaphragms are known in the art. The preferred diaphragm 28 is mode of an alloy sold under the trademarks KOVAR™ or INVAR 36™ by Hamilton Technology, Inc., of Lancaster, Pa. The diaphragm 28 is preferably approximately 12.5 µm to achieve optimum spot welding and sensitivity. Such a diaphragm is described in Baek S G. Ph.D. Thesis, University of Utah, (1992). The diaphragm 28 is preferably seal welded to the enclosure 20 between the semipermeable membrane 26 and the closed end 24 of the enclosure 20. The hydrogel 30 fills the chamber within the enclosure 20 between the semipermeable membrane 26 and the diaphragm 28. The means for measuring 40 and the means for reporting 60, described below, are located the chamber within the enclosure 20 between the diaphragm 28 and the closed end 24 of the enclosure 20.

Analyte Binding Molecules

Table I contains a list of analyte and analyte binding partners to which the method and biosensor of the invention can be applied. The analyte binding partner molecule should bind the analyte with sufficiently high specificity and avidity. For examples, an antibody (ABM) tightly bind with an antigen (analyte) with a high specificity.

TABLE 1

| Analyte Binding Molecule (ABM) | Analyte |
| --- | --- |
| Antibody | Antigen |
| Enzyme and Kinase | Cofactor, Substrate, and Inhibitor |
| Protein A | IGG |
| Concanavalin A | D-Sugar |
| Lectins | Carbohyrates |
| Boronic acid | 1,2-cis-Diol sugars |
| Thiol | Cystein |
| Receptors (Cell membrane receptors, Cytosol receptors, and Nuclear receptors) | Growth factors, Hormones, Metal ions, Modifed molecules such as phospholated. |
| Heparin, DNA, and RNA | Protamine, Polylysine, Polyarginine |
| Poly U, Poly A, Poly Lysine, and Poly Arginine | Nucleic acid |
| Triazine dye | Nucleotide |
| Commassie blue and Azure A | Arginine, Lysine, and Proteins |
| Metal binding molecules including chelating agents | Ca ion, Mg ion, etc |

Hydrogel Preparation—Charged Pendant Groups, Immobilized Analyte and ABMs

General methods for the preparation of hydrogels and polymer matrices including gels that are pH sensitive or have charged pendant groups are described in the literature: see for example Brondsted H et al Polyelectrolyte gels: Properties, Preparation, and Application, Harland R S., Prud Homme P K, eds ACS: 285, 1992; Ghandehari H et al 1996 J. Macromol. Chem. Phys. 197:965; and Ishihara K et al 1984 Polym. J. 16:625, the teachings of all of which are hereby incorporated by reference. Certain aspects of the making of pH-sensitive hydrogels are described also in the related copending applications PCT/US00/23194, pub. date Mar. 8, 2001, and U.S. Patent Applications Ser. Nos. 09/308, 392 and 09/824,552., the contents of which are hereby incorporated by reference The hydrogels contain, or can be modified to contain, diverse functional groups. These functional groups can be used by those skilled in the art to conjugate the ABM and analyte to hydrogel backbone. These functional groups include but are not limited to the following: carboxyl, hydroxyl, alkyl, hydroxylalkyl, oxyalkyl, oxyhydroxyalkyl, saccharide, carboxyl, carboxyamidealkyl, aromatic amino, phenolic hydroxyl, and polyethylene glycol. Coupling reactions include but are not limited to the following: diazonium coupling, isothiocyano coupling, hydrazide coupling, amide formation, disulfide coupling, dimethylacetyl coupling, maleic anhydride coupling, thiolactone coupling, and dichlotriazine coupling. These coupling reactions between two functional groups have been well documented and are considered well known to those skilled in the art. For example, a carboxyl group in the hydrogel can be covalently coupled to amino group in a peptide using coupling agents such as 1-ethyl-3-(3-dimethylaminoprophyl) carbodiimide hydrochloride (EDC) and dicyclohexylcarbodiimde. EDC activates carboxyl acid group which then reacts with an amino group in a peptide resulting in the formation of a covalent amide bond between the carboxyl acid group and the amino group. This has been shown in Anal Lett. 15, 147–160 1982, J. Biochem 92 1413–1424 1982.

A primary amino group in a peptide chain in ABM and analyte can also be conjugated to hydrogel containing a functional group (such as thiol, hydroxyl, acyl chloride, sulfate, sulfonyl chloride, phosphate, phosphate chloride, and imide) using coupling agents and/or cross-linking agents such as benzyl carbamate, carbonate, N-succinimidyl 3-(2-pyridyldithio) propionate (SPDP), sulfo-LC-SPDP, succinimidyl 4-(N-maleimidomethyl) cyclohexane-1-carboxylate (SMCC), sulfo-SMCC, m-maleimidobenzoyl-N-hydroxysuccinimide ester (MBS), sulfo-MBS, N-succinimidyl (4-iodoacetyl) aminobenzoate (SIAB), sulfo-SIAB, succinimidyl 4-(p-maleimidophenyl) butyrate (SMPB), sulfo-SMPB, dithiobis (succinimidylpropionate), 3,3'-dithiobis (succinimidylpropionate), disuccinimidyl suberate, bis (sulfosuccinimidyl) suberate, disuccinimidyl tartarate (DST), sulfo-DST, bis[2-(succinimidooxycarbonyloxy)ethyl]sulfone (BSOCOES), sulfo-BSOCOES, ethylene glycolbis (disuccinimidylsuccinate) (EGS), sulfo-EGS, etc. Other analytes and ABM which have several pendant functional groups such as thiol, hydroxyl, acyl chloride, sulfate, sulfonyl chloride, phosphate, phosphate chloride, and imide can also be conjugated to hydrogel chain using the above coupling agents and crossing-linking agents.

Concerning the charged moieties pendant from the hydrogel backbone, these are the source of the force which underlies the swelling of the hydrogel in response to the displacement of immobilized analyte from ABM partners. Thus, it will be apparent that whatever specific charged moieties are included, they must be present in amounts sufficient to provide a net charge. It does not matter whether the charge is negative or positive, but there must be a net charge.

In a preferred method of making the hydrogel, a vinyl group is attached to an analyte and ABM containing a functional group such as amine and hydroxyl group through etherification reaction with allyl alcohol and/or nuclearphilic reaction with methaacryloyl chloride. Copolymerization an analyte and ABM with cross-linking agents and monomers such as acrylamide and hydroxylethyl methaacrylate (HEMA) preferably forms with a free radical reaction. The polymer chain preferably contains chemically immobilized analyte and ABM as pendant groups. The hydrogel is preferably porous. The porosity is preferably controlled with several methods such as bubbling or excessive addition of powdered salt to the copolymerization reaction. The hydrogel preferably swells when free analyte is introduced in the hydrogel due to competitive binding to immobilized ABM on the hydrogel. The swelling ratio is preferably proportional to free analyte concentrations in the solution. The reaction ratio analyte and ABM, monomer, and cross-linking agents are preferably optimized to give a measurable pressure with a pressure transducer resulting in swelling and de-swelling of the hydrogel by changing free analyte concentrations.

It will be apparent that the range of changes in swelling tendency/osmotic pressure and thus the useful sensitivity to free analyte concentration will depend on the amount/proportion of immobilized analyte & ABM molecules in the hydrogel, as well as on the amount and/or distribution of excess charge (net positive or negative charge) carried by the pendant charged moieties. The amounts and proportions of these three key components may also depend to some extent on the nature of the specific analyte. In any case, knowing the principles of the measurement method and device of the invention and general chemical synthetic methods for such hydrogels, optimal levels of the three components can readily be determined for any analyte of interest.

Glucose Biosensor

A specific example of a biosensor of the invention is a glucose biosensor, described in the related application PCT/US00/23194, pub. date Mar. 8, 2001, the contents of which are hereby incorporated by reference. In the glucose biosensor, the analyte binding partner is concanavalin A.

Means For Pressure Detection

The biosensor includes a means for measuring 40 the pressure of the hydrogel. This element is critical. A biosensor 10 that directly relies on change in free analyte concentration avoids an important source of outside interference. Free analyte itself is a controlled parameter than parameters measured directly by electrodes.

Figure 6:
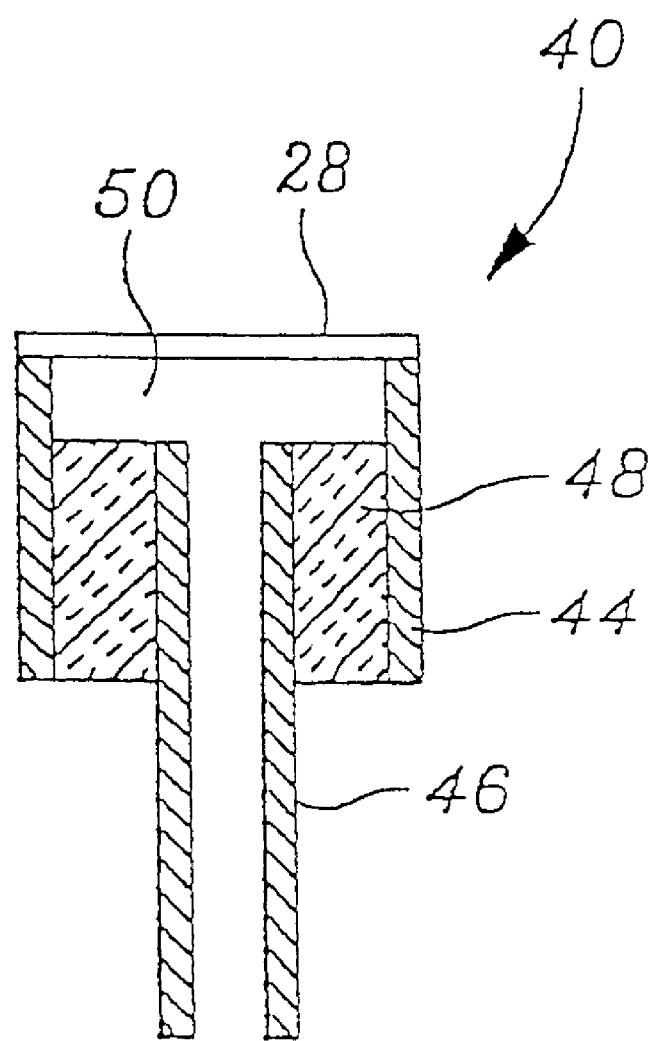
FIG. 6 is side elevational sectional view of the pressure transducer.
Figure 7:
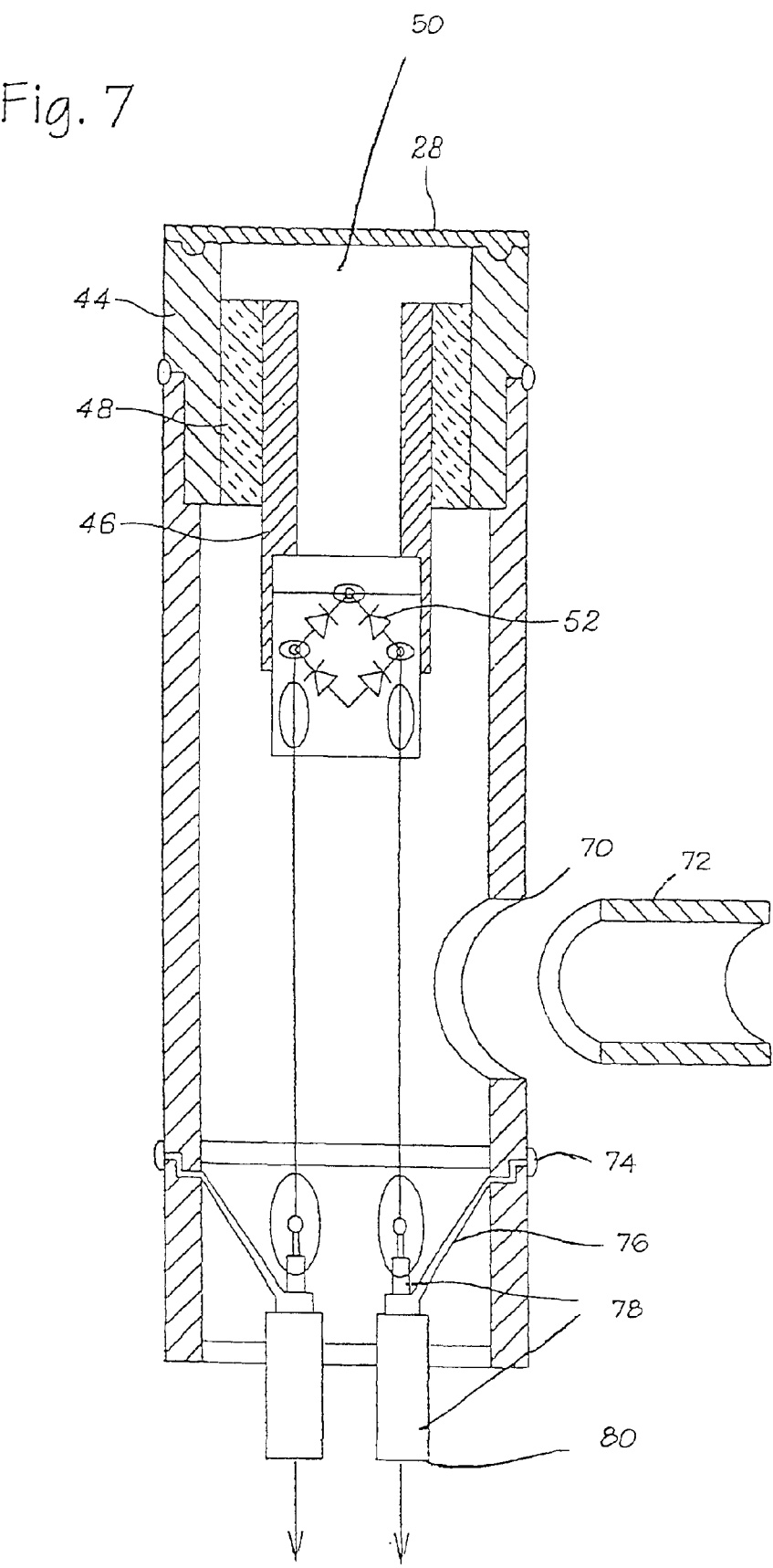
FIG. 7 is side elevational sectional view of the pressure transducer including the preferred circuit board having miniature diodes, which are part of a diode quad bridge circuit.
Figure 8:
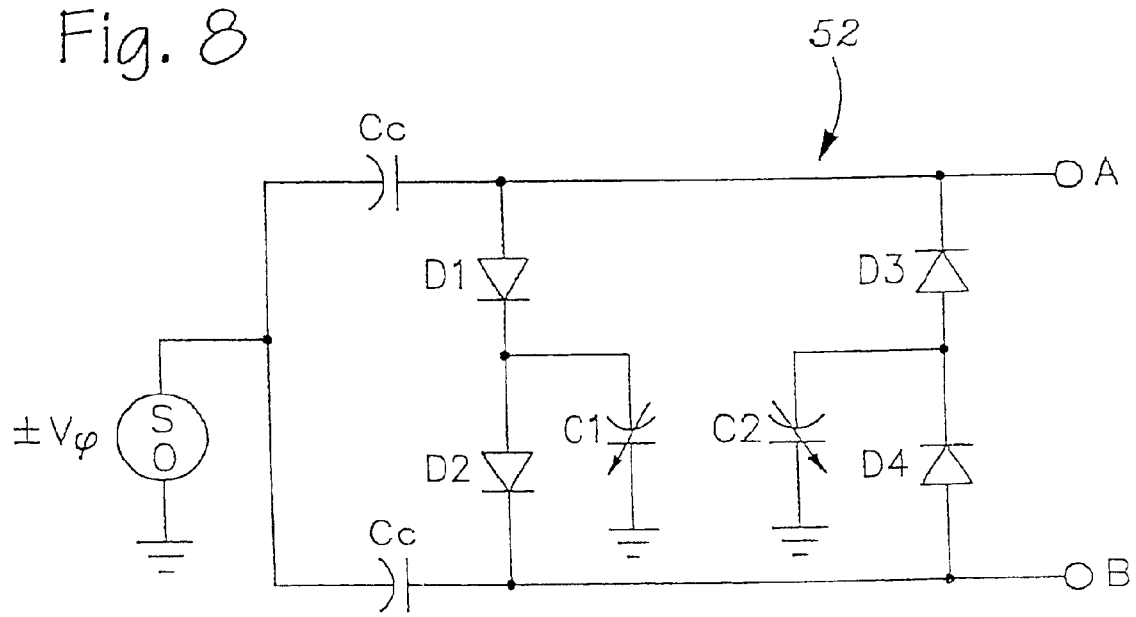
FIG. 8 is an electrical schematic showing the preferred diode quad bridge circuit.

As shown in FIGS. 6–7, the means for measurement is preferably a pressure transducer 40. Pressure transducers are known in the art and those skilled in the field can construct a transducer optimized to the specific needs of the biosensor 10. An example of a transducer is disclosed in Harrison D R, Dimeff J. Rev. Sci. Instrum. 44:1468–1472, (1973) and Harrison et al., U.S. Pat. No. 3,869,676, titled Diode-Quad Bridge Circuit Means, hereby incorporated by reference.

As shown in FIG. 7, the biosensor 10 can also include a calibration hole 70 which receives a small brass tube 72, a solder stranded copper wire 74, a braided shield 76, insulators 78 and coaxial cables 80.

In its most preferred embodiment, the means for measuring 40 is a capacitive pressure transducer 40 associated with the flexible diaphragm 28 described above. The preferred transducer 40 includes a first electrode 44 and a second electrode 46, the first and second electrodes 44 and 46 being separated by an insulator 48. In its preferred embodiment, the first and second electrodes 44 and 46, as well as the insulator 48, are coaxially aligned cylinders. The flexible diaphragm 28 is preferably welded to the top of the first conductor 44, converting the diaphragm 28 into one of the electrodes of a capacitor portion of the transducer 40. The first electrode 44 is connected to the diaphragm 28, and the diaphragm 28 is separated from the second electrode 46 by an air gap 50.

Since the diaphragm 28 is in mechanical contact with the hydrogel 30, the diaphragm 28 deflects in response to changes in the pressure of the hydrogel 30, thereby changing the size of the air gap 50 between the second electrode 46 and the diaphragm 28, thereby changing the value of the capacitance. The value of the capacitance change is detected remotely, preferably using a diode quad bridge circuit 52. These pressure transducers 40 have been successfully used to measure pressure changes in flowing polymeric liquids as small as one Pascal.

Examples of alternative transducers are described in Takaki, U.S. Pat. No. 5,711,291 and Fowler, U.S. Pat. No. 5,752,918, hereby incorporated by reference. A more detailed discussion of transducers can be found in the following references, hereby incorporated by reference: Baek S G. Ph.D. Thesis, University of Utah, (1991); Magda J J, Baek S G, Larson R G, DeVries K L. Polymer 32:1794–1797, (1991); Magda J J, Baek S G, Larson R G, DeVries K L. Macromolecules 24:4460–4468, (1991); Magda J J, Lou J, Baek S G. Polymer 32:2000–2009, (1991); Lee C S, Tripp B, Magda J J. Rheologica Acta 31:306–308, (1992); Lee C S, Magda J J, DeVries K L, Mays J W. Macromolecules 25:4744–4750, (1992); Magda JJ, Baek SG. Polymer 35:1187–1194, (1994); Fryer T. *Biotelemetry III*, Academic Press, New York, pp.279–282, (1976); Tandeske, D., Chapter 5 in Pressure Sensors Selection and Application, Marcel Dekker, New York, 1991; Updike S J, Shults M C, Rhodes R K, Gilligan B J, Luebow J O, von Heimburg D. ASAIO J. 40:157–163, (1994); and Foulds N C, Frew J E, Green M J. Biosensors A Practical Approach (Cass AEG. eds.) IRL Press Oxford University, pp. 116–121, (1990).

While a preferred pressure transducer 40 has been described, those skilled in the art can devise other means for measuring 40. Other alternative embodiments include a piezoelectric transducer and a piezoresistive pressure sensor. Other means for measuring pressure or increase in volume could also be used. These alternatives are considered equivalent to the described invention.

Means For Reporting—Telemeter

Figure 4:
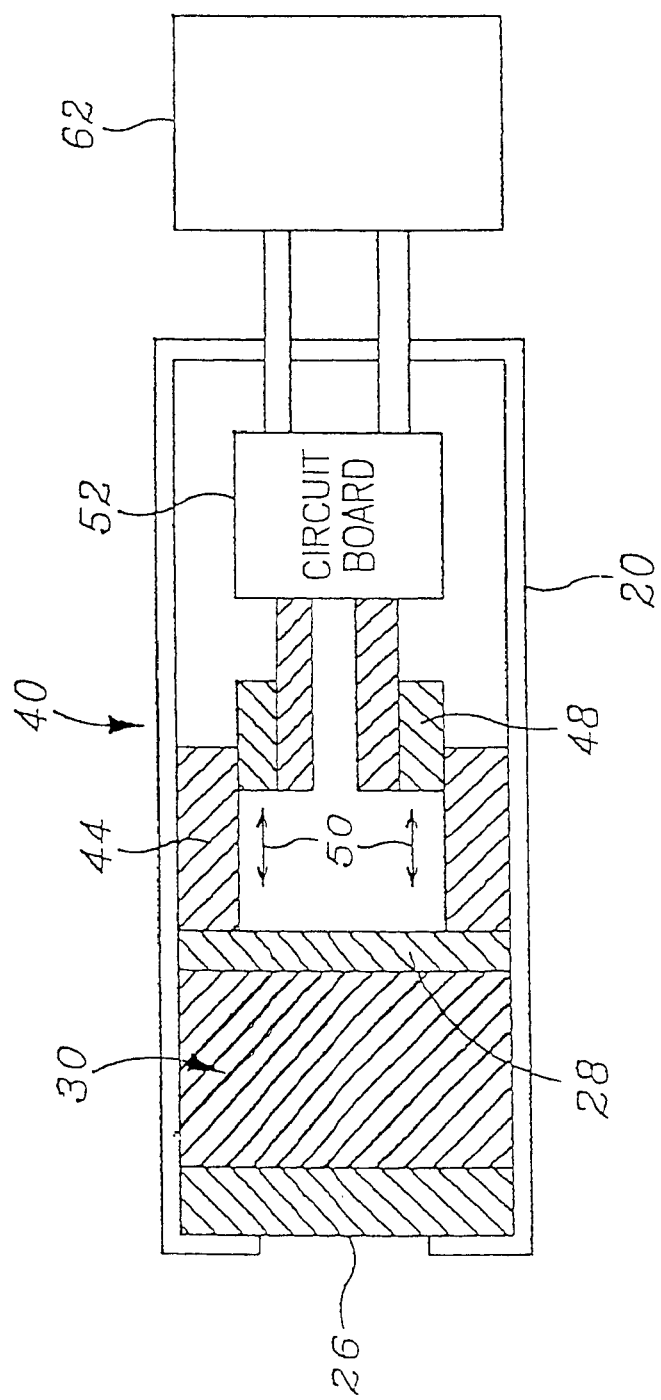
FIG. 4 is a side partial cross-sectional view of an alternative embodiment thereof, showing a biosensor that is electronically attached to a computer.

Finally, the biosensor 10 includes a means for reporting 60 the concentration of the analyte molecule once it has been measured. This element will vary greatly depending upon the specific use of the biosensor 10 as well as the needs of the user. In its simplest form, as shown in FIG. 4, the transducer 40 is simply connected electronically to a computer means, generally a personal computer. The computer compares the data from the transducer 40 to a calibration curve to generate usable data for export through a reporting means. In one embodiment, the computer sounds an alarm if the concentration of the analyte molecule exceeds a certain level. In another embodiment, the computer outputs data onto a reporting outlet such as a computer monitor. In yet another embodiment, the computer controls a feedback loop to change a process is response to variation in the concentration of the analyte molecule.

In a preferred embodiment, as shown in FIG. 3, the biosensor 10 is a biosensor 10 that can be implanted into the human body. In this case, the means for reporting 60 is preferably a battery powered telemeter 60 that transmits a data signal to a receiver operably connected to the computer. The computer also compares the data signal to a calibration curve and reports the concentration through a reporting means. The reporting means is preferably an audible alarm to warn patients if analyte levels get too high or too low.

Method For Using A Biosensor

Figure 5:
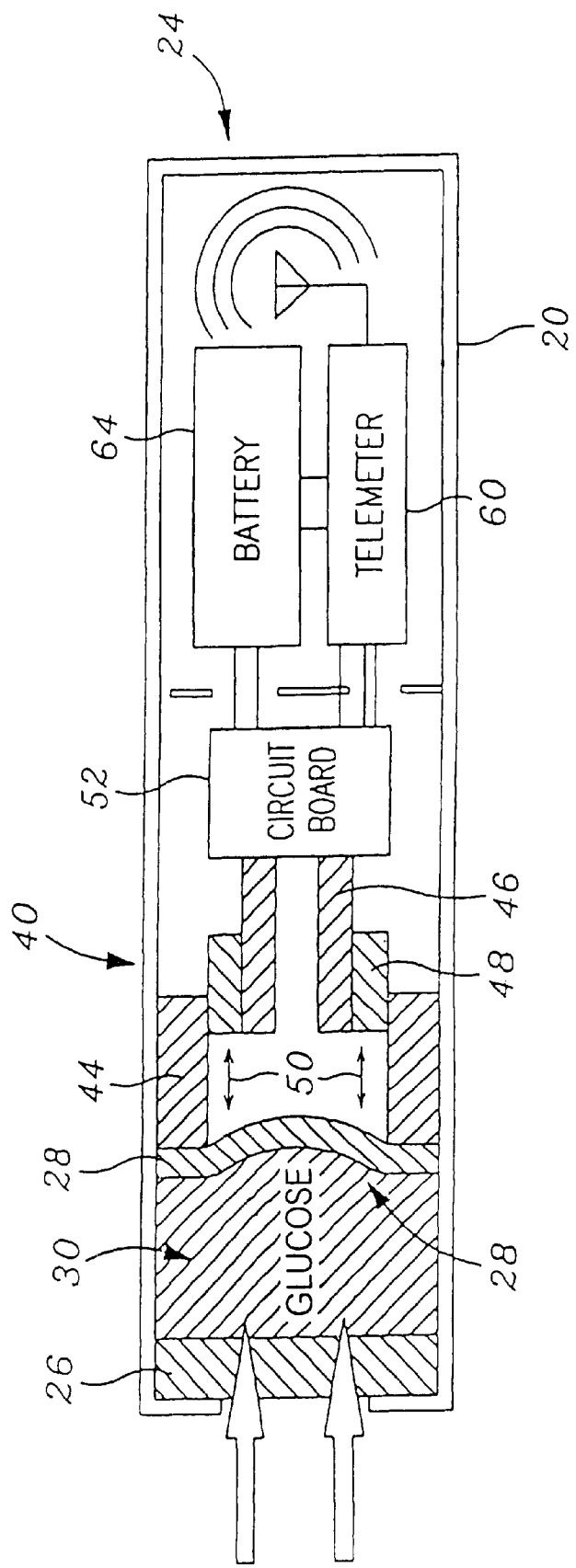
FIG. 5 is a side partial cross-sectional view of the preferred embodiment, showing analyte diffusing into the hydrogel, causing the hydrogel to swell and causing the pressure transducer to signal to a computer through a telemeter.

The invention further includes a method for using a biosensor 10 to measure the concentration of analyte in a solution. The method includes the following steps: First, providing a biosensor 10 as described above. ABM is chemically or physically immobilized in the hydrogel 30, preferably using chemical conjugation. The biosensor 10 is preferably first immersed on a buffer and inserted into a control solution. The data generated is then compared to a calibration curve to calibrate the biosensor 10. Once the biosensor 10 is removed and rinsed in another buffer, the biosensor 10 is inserted into the solution. The analyte molecules are allowed to diffuse into the polymeric hydrogel 30, causing the competitively binding of free analyte with immobilized analyte to ABM. The competitive binding between free analyte and immobilized analyte to ABM causes the hydrogel 30 to increase in osmotic pressure and swell, as shown in FIG. 5. This swelling is measured with the means for measuring 40. The means for measuring 40 is preferably a pressure transducer 40. The pressure transducer 40 is used to measure the osmotic pressure of the hydrogel 30, which is proportional to the concentration of the free analyte level in the hydrogel 30. Data from the transducer 40 regarding this measurement is then sent to a means for reporting 60. In an implantable biosensor 10, a battery powered telemeter 60 is used to transmit the data to a computer. This can be then reported to the user through a computer monitor, an audible alarm, or a feedback system. Throughout use, the system can be recalibrated by taking blood samples and comparing the analyte readings to those reported by the biosensor 10. The computer actuated means of calibration can then be adjusted to correct for any errors.

While the invention has been described with reference to at least one preferred embodiment, it is to be clearly understood by those skilled in the art that the invention is not limited thereto. Rather, the scope of the invention is to be interpreted only in conjunction with the appended claims.

Operation Principles of the Health Alarm System

The output of a sensor is always monitored and compared with a preset value (or threshold value). If the sensor output is out of the preset range, an alarm signal is generated. This alarm signal can be further utilized to actuate a certain alarm protocol such as automatic dialing and send a prerecorded message corresponding to the condition detected.

Figure 9:
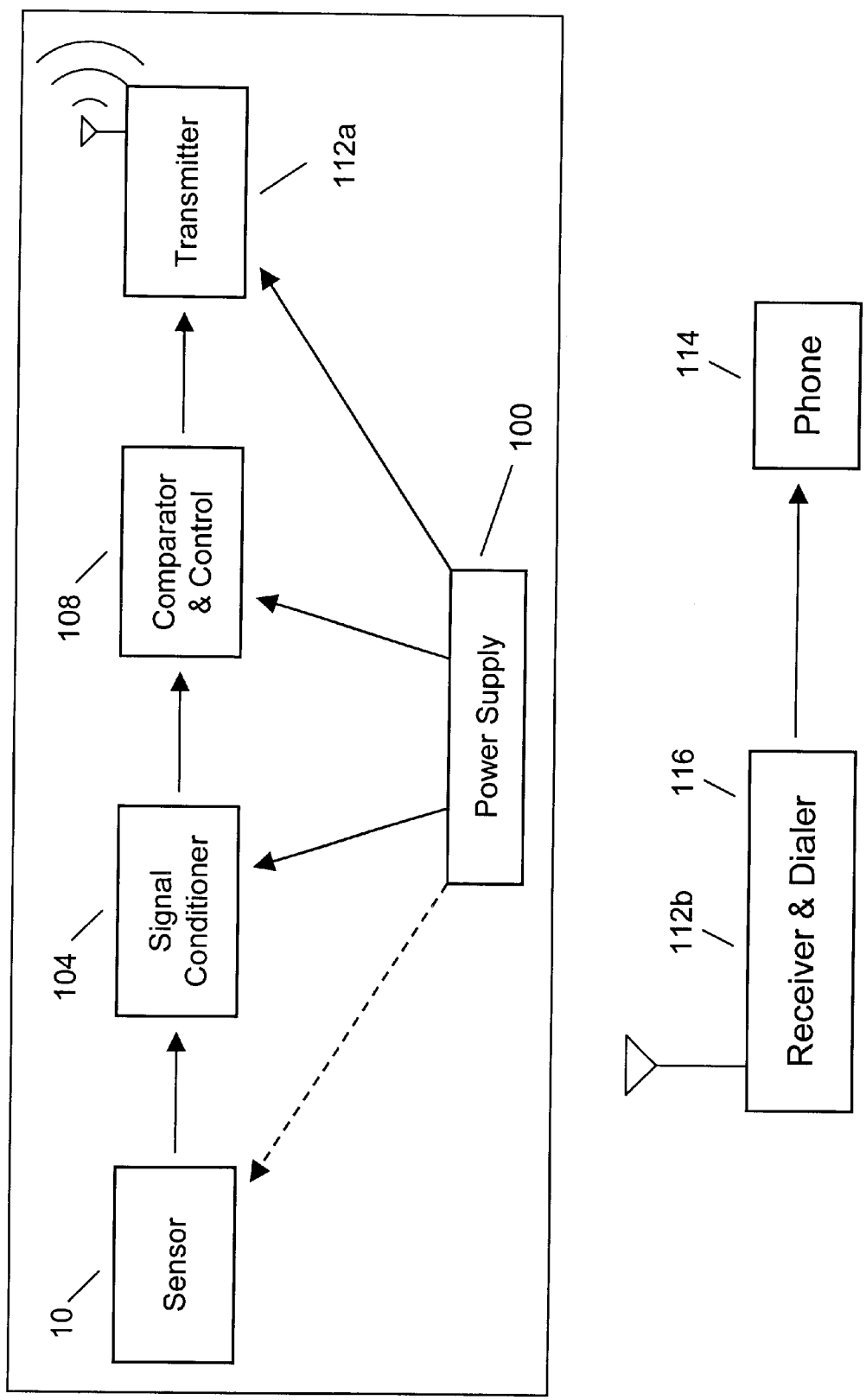
FIG. 9 is a block diagram of one embodiment of an automatic alarm system in conjunction with wireless actuation of dialing.
Figure 10:
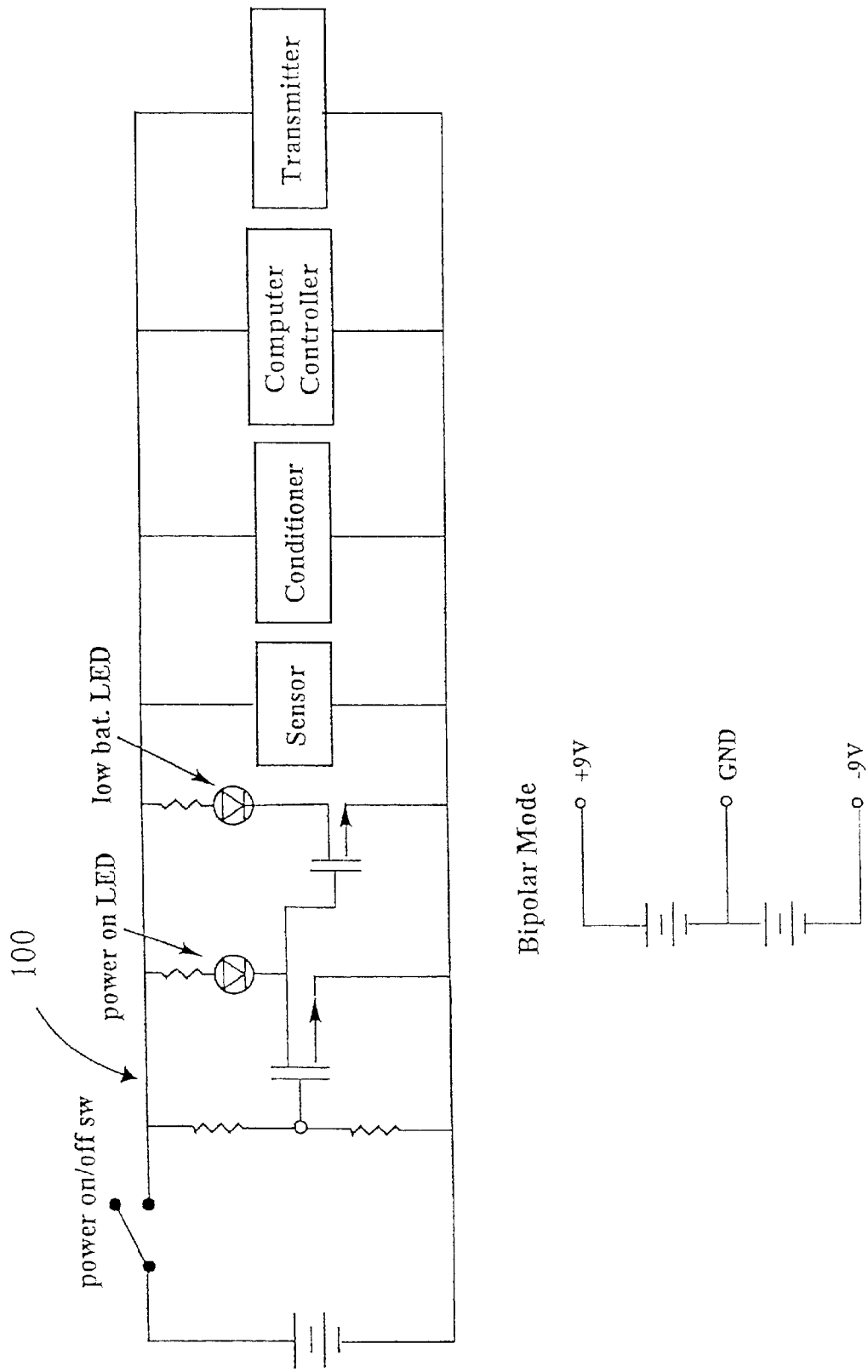
FIG. 10 is a schematic diagram of a power supply for the various portions of the automatic alarm system of FIG. 9.
Figure 11:
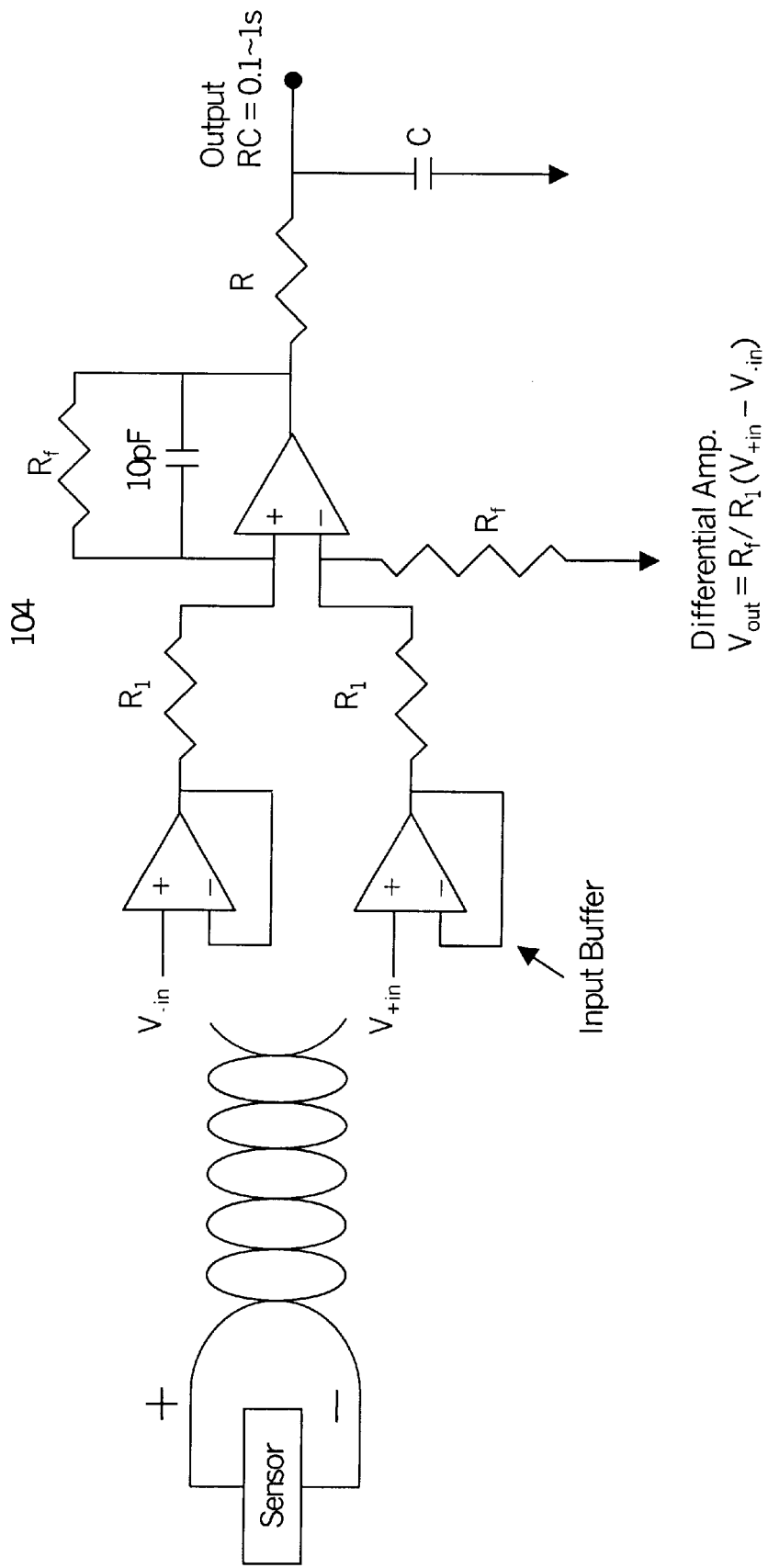
FIG. 11 is a schematic diagram of the signal conditioning circuit of the alarm system of FIG. 9.

The block diagram in FIG. 9 shows a diagram of a working model for giving an alarm to diabetics and a signal to caretakers using automatic dialing and sending of a prerecorded message when blood glucose levels drop to the level of hypoglycemia.

In one embodiment, depicted in FIGS. 9–15, the major elements of an automatic alarm device are a power supply 100, a sensor (such as biosensor 10 or other sensor for monitoring a physiological condition), a signal conditioning circuit 104, a comparator circuit 108, a transmitter/receiver 112a and 112b, a dial actuator 116, and a control circuit.

The power supply 100 preferably provides electric energy to all the elements of the device requiring power. Considering portability of the device, a dry-cell battery is the preferred choice for supplying power. However, compatibility of the cell with power requirements of all the elements (voltage and capacity) will be somewhat determinative of the type used. As presently perceived, a large capacity 9-volt battery is believed to be the best choice. However, during the development, a bipolar power supply using 2 batteries makes the circuit design much easier. A low-battery indicator should be an essential part.

The need for the signal conditioning circuit 104 depends on the quality of the signal from the sensor. If the sensor signal comes along with a great deal of environmental noise, the signal conditioning circuit 104 (FIG. 11) is necessary to operate the device in a reliable manner. Typically, a high input-impedance differential amplifier works for any kind of sensor. A prepackaged circuit, the so-called "instrumentation amplifier" is commercially available. However, for a prototype device, a quad-op amp IC (e.g., LM 384 from National Semiconductors) will serve well by providing 4 amplifiers. A differential amplifier is excellent in removing common mode noise. The gain of the differential amplifier can be adjusted to provide signals of a good linear range. A low-pass filter after differential amplification will further decrease high frequency noise. An RC time constant of 0.1 to 1 seconds is appropriate. For example, an RC time constant of 1 second can be obtained using 100 kohm and 10 mF.

In the embodiment of FIGS. 9–15, a comparator always compares the monitored signal (here, from the output of the signal conditioning circuit) with the preset value. The threshold value will be adjusted using a potentiometer. If the monitored signal goes over the threshold value, the output of the comparator changes its status from '0' to '1' or from 'off' to 'on'. This change of status is utilized to actuate a following digital circuit. The simplest circuit will be driving an electromechanical switch to 'on' position, by which a transmitter circuit is connected to the power supply; LM311 type comparator should best fit the purpose.

Figure 12:
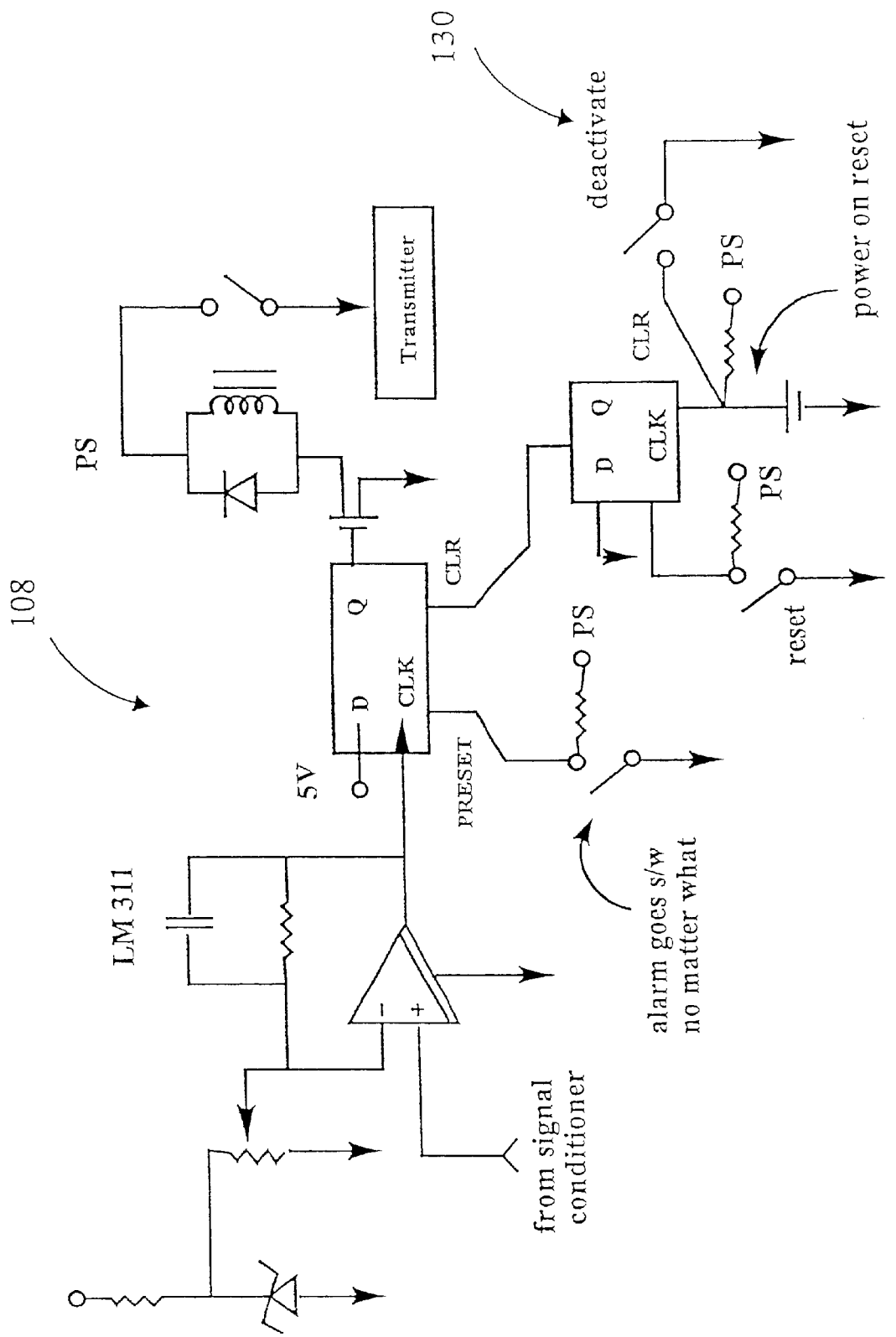
FIG. 12 is a schematic diagram of the comparator and control circuit of the alarm system of FIG. 9.

The comparator circuit 108 must be with extra control circuits 130 (FIG. 12). The extra controls are for deactivating the device and resetting the device in the case when alarms are sent mistakenly or by device malfunction. Furthermore, an extra switch should be there to actuate dialing in any case at the discretion of the device user. All these factors can be achieved by using a digital D-flip-flop IC(C7474)

If necessary, the comparator circuit 108 can be used for determining if the sensor 10 operates normally as well as for alarming. If sensor output goes beyond an expected operating range including an alert level, the comparator 108 will indicate malfunction of the sensor 10.

Figure 13:
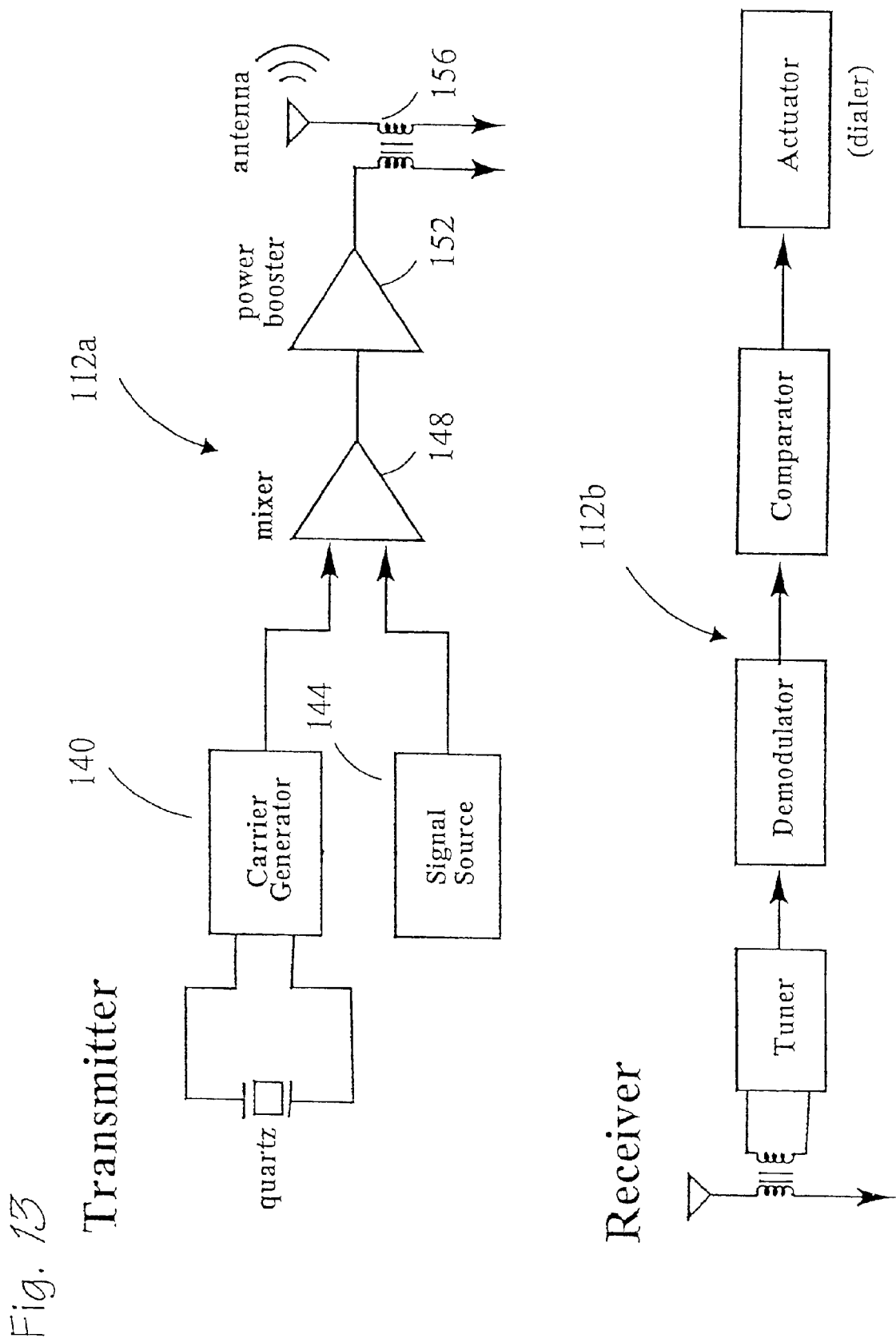
FIG. 13 is a schematic diagram of the transmitter and receiver of the alarm system of FIG. 9.

A transmitter/receiver 112a and 112b is necessary in order to operate a phone 114 at a distance from the device-carrier (FIG. 13). Wireless activation of the phone 114 can be achieved using a typical FM method. Typically, a transmitter consists of a carrier wave generator 140, a signal generator 144, a modulator 148 to mix signal to carrier wave, a power booster 152, and a radiator 156. The carrier wave frequency may be in the range of several tens to several hundreds megahertz. The signal must be unique that the receiver picks up to avoid mistaken dialing due to environmental noises from other electronic devices. A receiver 112b operates in a reversed manner to that of a transmitter 112a. Although a transmitter/receiver, 112a/112b must be custom designed eventually, it can be adapted from a minimally modified transmitter/receiver used in kids' remote control toys. (In light of the present disclosure, those skilled in the art will appreciate that other forms of remote communication, such as electronic mail could also be used.)

Figure 14:
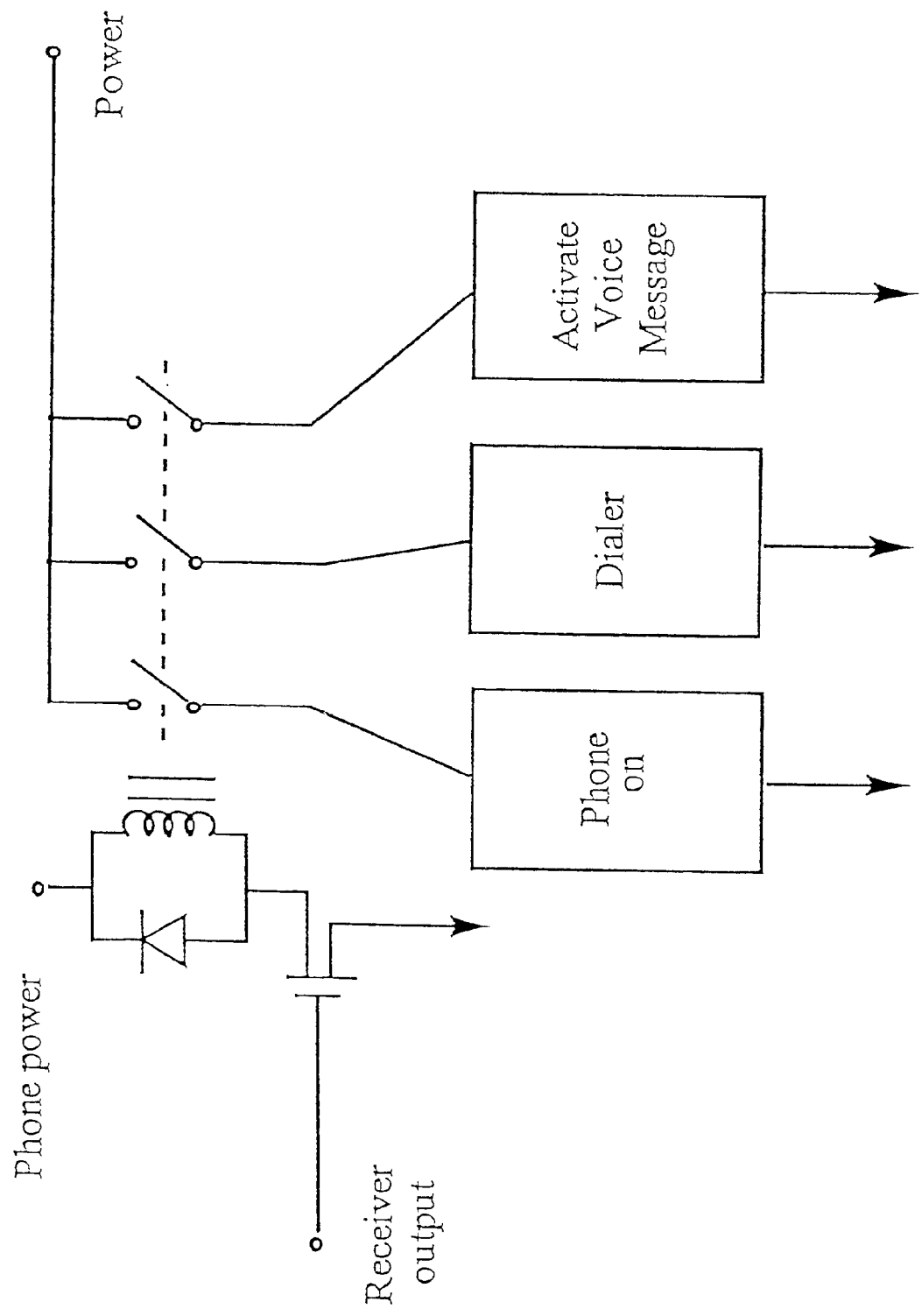
FIG. 14 is a schematic diagram of a dialing mechanism of the alarm system of FIG. 9.

Dialing to a remote alarm signal can be achieved in a number of ways that will be well known to those skilled in the art. A schematic of such a system is shown in FIG. 14 and those familiar with remote telephone interactions will be familiar with numerous ways of implementing this and other configurations.

Some degree of modification is necessary to allow utilization of current answering phone systems, and utilization of current answering function to dialing/messaging. Overall, everything is preferably prepared in the phone. It simply needs a sort of switching on by an alarm signal from the receiver.

Figure 15:
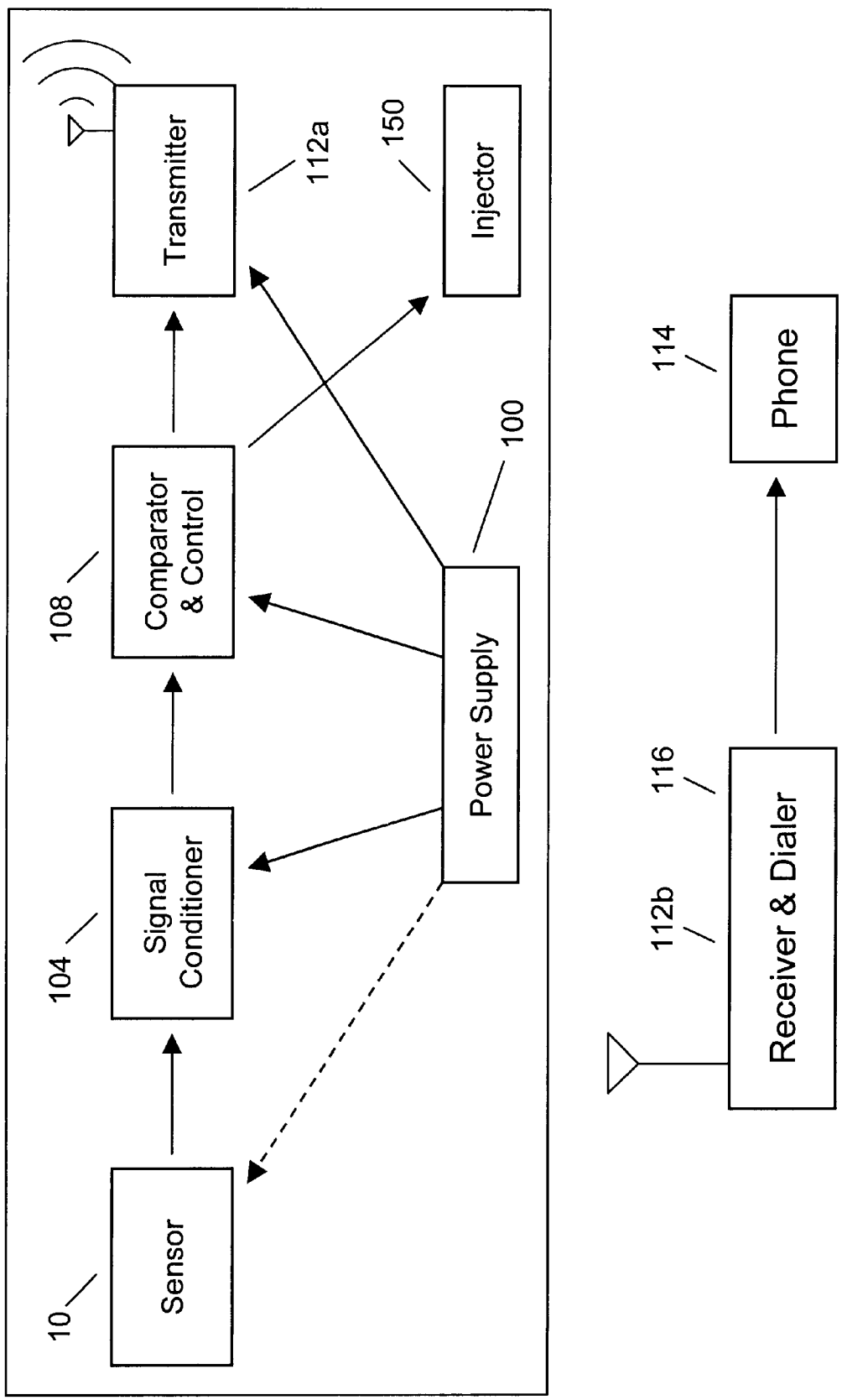
FIG. 15 is a block diagram of an automatic alarm system of FIG. 9 used in conjunction with an injection device for providing injections responsive to the alarm system.

In addition to the above, the alarm system can also function as a system for treating hypoglycemia in a diabetic. Turning to FIG. 15, there is shown a schematic of an alarm system similar to that shown in FIG. 9. The system further includes, however, an injection mechanism 150 that dispenses glucose, another sugar, or a drug into the blood stream of the patient in response to the alarm. Those skilled in the art will appreciate that the injection device 150 may provide predetermined dose, or may inject varying quantities in response to the physiological condition detected by the sensor 10. The injection device 150 may be hard wired to the system, or may be controlled by the transmitter 112a.

In addition to the injection mechanism 150, the system can also include a global positioning system 160 associated with the telephone 114 or some other position of the alarm system. The global positioning system 160 enables rapid location of the individual in the event that medical treatment is necessary. Such a system is particularly beneficial for individuals who have diabetes but still which to engage in activities such as cycling, hunting and fishing.

Alternate Embodiment—FIGS. 16–23

Figure 16:
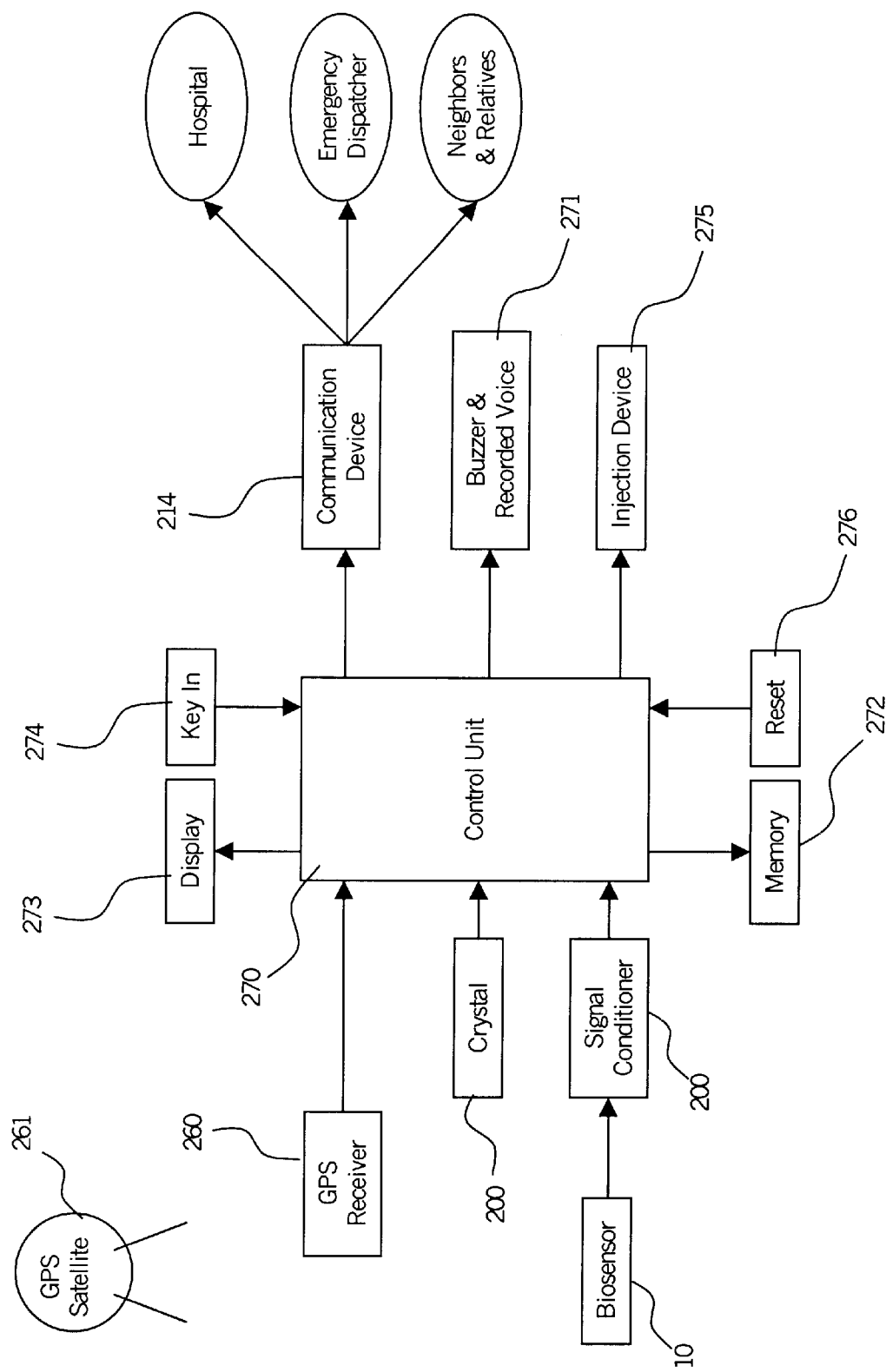
FIG. 16 is a block diagram of a highly preferred embodiment of an automatic health alarm system.
Figure 17:
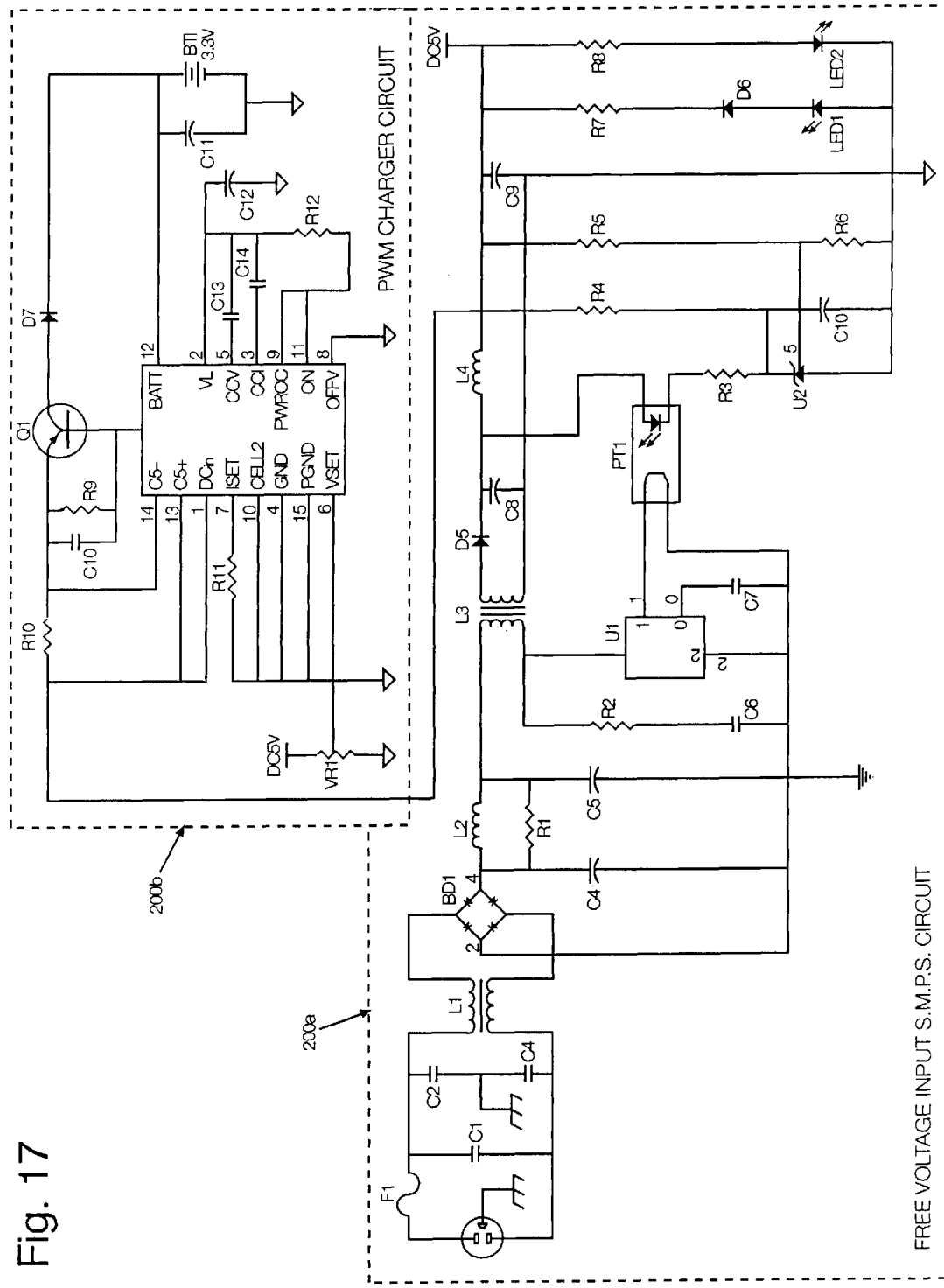
FIG. 17 is a power supply circuit for the alarm system embodiment of FIG. 16.
Figure 18:
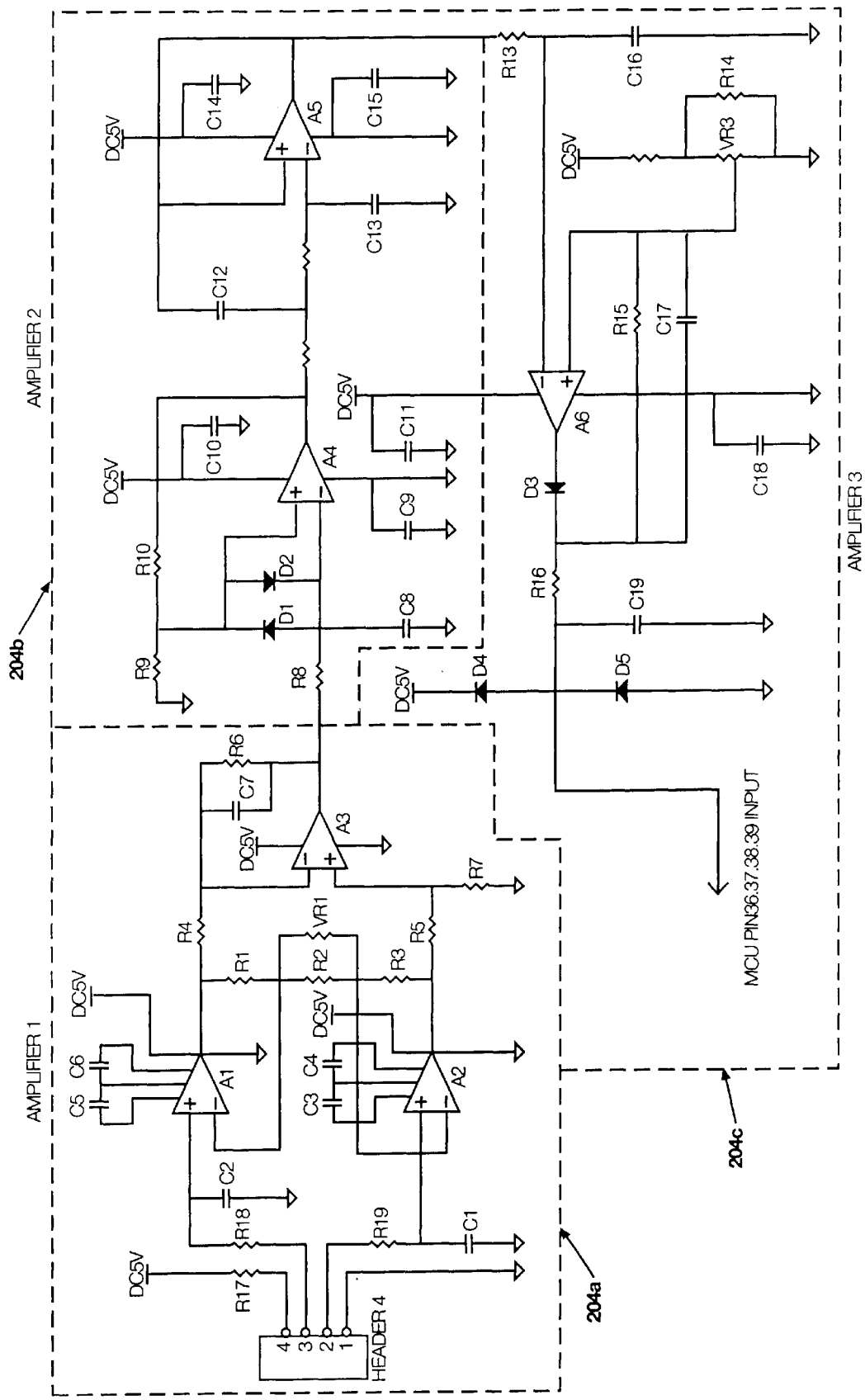
FIG. 18 depicts a signal conditioning circuit for the alarm system of FIG. 16.
Figure 19:
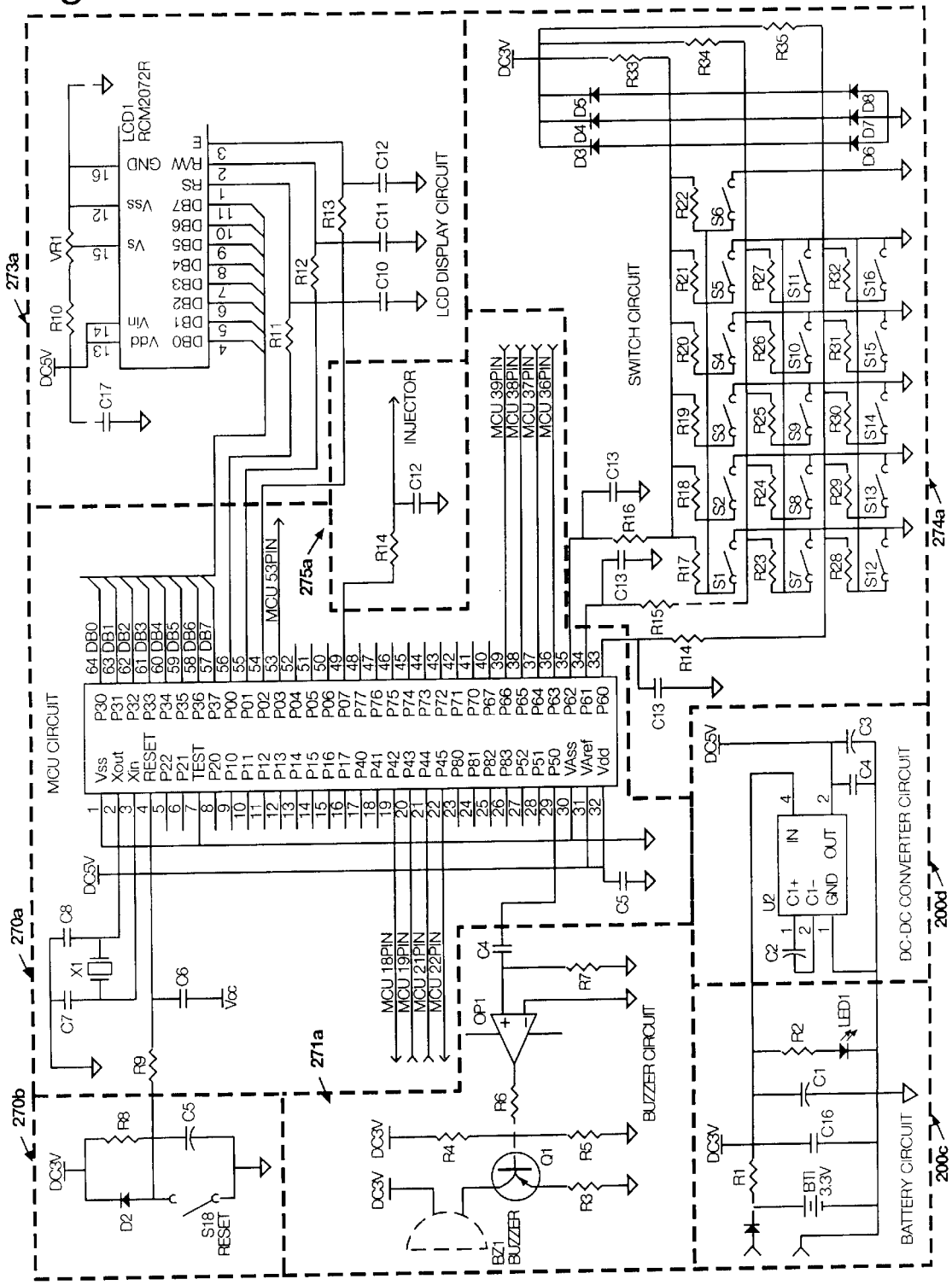
FIG. 19 depicts a circuit for a micro-control unit of the alarm system of FIG. 16.
Figure 20:
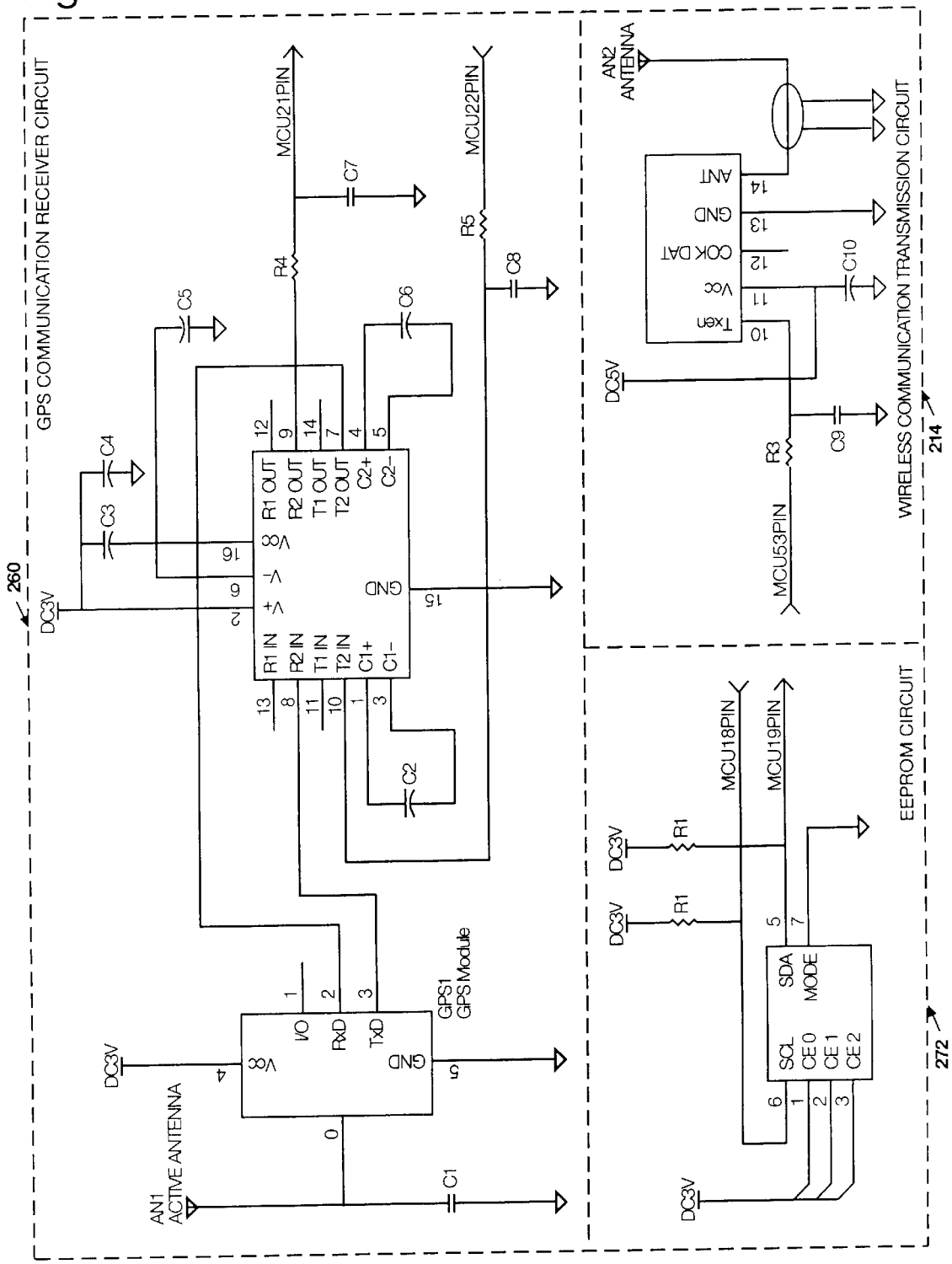
FIG. 20 depicts circuits for the GPS and communications transmitters of the alarm system of FIG. 16.

A highly preferred embodiment of the automatic alarm system is depicted in FIG. 16, and circuits useful in this embodiment are shown in FIGS. 17–23. As seen in FIG. 16, the major elements are a sensor (such as biosensor 10 or other sensors for monitoring physiological condition), a power supply 200, a signal conditioning unit 204, a global positioning system (GPS) receiver 260, a MCU circuit unit 270, and a data transmitter 214.

The power supply 200 preferably provides electric energy to all the elements of the device requiring power. Considering portability of the device, a battery is the preferred choice for supplying power. However, compatibility of the cell with power requirements of all the elements (voltage and capacity) will be somewhat determined of the type used. As presently perceived, a +3.3-volt (+3.3V) rechargeable battery and a charging system are preferably used to supply power as a whole.

For a battery charger, SMPS (Switching Mode Power Supply) 200a is preferably used to convert an AC input voltage of free range about AC 85V to AC 265V into constant DC voltage of +5V. By using of the output DC voltage from SMPS, charging circuit 200b charges the rechargeable battery according to the battery capacity and remaining battery level. In this charging system, Li-ion, Ni-ca, and Ni—H are preferably used for the rechargeable battery 200c. A low battery indicator and a charging status indicator should be an essential part.

The rechargeable battery can be charged up to +3.3V, which is supplied to the circuit as a whole except the LCD and the transmitter and micro controller unit (MCU). Additional +5V is needed to operate LCD and transmitter, and this voltage is preferably acquired from the battery by using of a conventional DC—DC converter 200d.

The need for the signal conditioning unit 204 depends on the quality of the signal from a sensor. If the sensor signal comes along with a great deal of environmental noise and/or a low voltage input, the signal conditioning circuit 204 (FIG. 11) is necessary to operate the device in a reliable manner. A signal-conditioning unit 204 is designed for a noise reduction and amplification for an input signal from a sensor. A prepackaged multi-step amplification circuit, the so-called "instrumentation amplifier" is commercially available.

However, for a prototype device, a chopper-op amp IC (e.g. MAX 420 or MAX421 from Maxim) and/or a quad-op amp IC (e.g., LM 384 from National Semiconductors) will serve well by providing multiple amplifiers for amplification of a low voltage signal without noise. A differential amplifier is excellent in removing common mode noise. A low-pass filter after differential amplification will further decrease high frequency noise. An RC time constant of 0.1 to 1 seconds is appropriate. For example, an RC time constant of 1 second can be obtained using 100 kohm and 10 mF.

A chopper-stabilized amp IC (A1, A2, A3, A4, A5, and A6 in signal conditioning circuit 204) preferably use for a prototype device in signal conditioning circuit. The op-amps are a monolithic chopper op-amp having precise input characteristics. Typically, a high input-impedance differential amplifier as a buffer circuit such as A1 and A2 in amplification circuit 204a works for any kind of sensor to adjust zero crossing with an available resistor like VR1 (a variable resistor) in amplification circuit 204a. A1 and A2 preferably have voltage-regulating capability with condensers such as C3, C4, C5, and C6 having a capability of chopping frequency of about 400 Hz to make a linear amplification. C1, a Mylar capacitor, is for the reduction of a signal noise, and VR1 is adjusted to make $V_{out}$ zero crossing. Condenser C7 decreases a gain in high frequency and reduces a noise.

The first amplification circuit (A3) 204a consists of a low pass filter for reduction of noise and an amplifier. The low pass filter reduces a level of noise before amplification. A3 204a as a chopper stabilized operational amplifier amplifies the filtered sensor signal. For a low voltage signal, the operational amplifier A3 preferably has a low input offset voltage of 1 $\mu$Vtyp and a low drift offset of 0.02 $\mu$V/Ctyp. The matching rules of the amplification circuit are R1=R3, R6/R7=R4/R5, Gain=$(1+2R1/R_x)*R6/R4$, and $R_x$=(VR1*R2)/(VR1+R2).

The second amplification circuit 204b consists of a second low pass filter (R12 and C13), a buffer circuit (A5), and an amplifier (A4) used to reduce broadband of a device noise. Since resistors R9 and R10 determine the reliability of gain (=1+R10/R9), they are preferably +/−1% of tolerance with low temperature coefficient. D1 and D2 are diodes for a circuit protection to high voltage input.

The final segment of the signal condition circuit 204c preferably provides a function of offset compensation (VR2 and VR3) and third amplification (A6 in circuit 204c). A condenser C17 is preferably selected to make a loop response critically damped. When the signal overshoot and a noise level are greater than input voltage $V_{cc}$, the input voltage $V_{cc}$ is preferably bypassed in the forward direction of a diode D4. When the signal overshoot and a noise level are less than ground voltage, input voltage $V_{cc}$ is preferably bypassed in the backward direction of diode D5.

The functions of the control unit are to compare the input sensor signal with the pre assigned reference signal, to determine the alarm status, to store new value of sensor signal, to retrieve the stored values in memory, to engage with data transmitter for emergency contact, to activate injection device, to initiate alarming buzzer, and to respond key input from patients.

As a primary control device in the automatic alarm system, an 8-bit microprocessor is preferably used for every transaction of the automatic alarm system. An assembler and/or a computer language like C language preferably code the transaction, which is compiled for the implementation of microprocessor in hand. Alarm status, GPS location code, and signal itself from a sensor can be stored in the memory semiconductor such as flash memory, SRAM, DRAM, or EEPROM. 8K byte of EEPROM 172*a* is preferably selected for the purpose.

The primary function of the microprocessor is to establish real-time monitoring and automatic alarm informing system. An 8-bit microprocessor having low power consumption can supervise the real-time monitoring activity and the automatic alarm system. TMP87CH48 of TOSHIBA 270*a* is preferably selected for the purpose.

Patients can manually operate the automatic alarm device by pushing the key such as reset, signal value display, location code display, and other assigned user functions. The control unit recognizes and interprets key input of a voltage level depending on which key users hit to accomplish the function in hand. The display with a displaying capacity of 20 characters and 2 lines is preferably TN type of LCD or RCM2072R of ROHM 273*a*. The extra control functions are the deactivation of the device and the reset 270*b* of the device in a case when alarms are sent mistakenly or by device malfunctions.

In emergency, the control unit has the facility to provide output pulse signal 275*a* to initiate an injection device, and activates an alarming buzzer 271*a*. The injection device is activated when the microprocessor turns on analog output circuit from 'high' to 'low' or 'low' to 'high' as a function '0' and '1'.

Through the monitoring functions of the control unit, patient's information is preferably continuously transferred to data transmitter in case of emergency. The patient's information preferably includes patient's code of identification, alarm status, GPS location code of X,Y,Z, and a current physiological value from a sensor.

Those skilled in the art will appreciate that the combination of a biosensor, an automated alarm notification system (GPS), and an emergency treatment system (an automatic injection system) provide significant advantages for improving health care. Not only is the patient warned of a condition, which can cause physiological damage, but also health care workers are notified with the updated location information of the patient if the situation surpasses a predetermined threshold.

A transmitter 214*a* is necessary in order to operate a communication device 214. The candidate for data transmitter 214*a* can be a communication devices 214 such as a phone including a portable wireless communication device, which can accommodate external data port for exchanging data with the automatic alarm system and inform alarm status and data automatically to a pre-determined devices in remote location. Cable and connector can preferably make the connection between data transmitter and automatic alarm system. The selection of cable and connector depends on the wireless data communication device in concern. In addition, a wireless connection protocol like Bluetooth can accomplish the data transfer between the devices.

Alarm status, location information, and other essential information from the automatic alarm system can be transmitted in the form of voice message or text message depending on devices in remote.

The wireless communication device is preferably a wireless personal phone supporting CDMA, TDMA, GSM, and other wireless communication standards in operation. PDA (Personal Digital Assistance) with remote Internet service can preferably be other form of wireless portable communication device.

Typically, a transmitter 214*a* consists of a carrier wave generator, a signal generator, a modulator to mix signal to carrier wave, a power booster, and a radiator. The carrier wave frequency may be in the range of several tens to several hundreds megahertz (MHz). The signal picked up from a receiver must be unique to avoid mistaken transmittal due to environmental noises from other electronic devices. Either AM or FM wireless communication can be applied in the automatic alarm system, employing the appropriate communication protocol, and matching an AM or FM receiver also designed to receive the data from the transmitter 214*a*.

The primary function of the GPS unit is to provide location data to the recipient(s) of the alarm in the event that the patient carrying the automatic alarm device either does not know his/her location or is unconscious or otherwise unable to describe his location.

A GPS receiver 260*a* supporting NMEA protocol is preferably used in the automatic alarm system. The receiver gives a location coordinate of X, Y, Z in a binary form, and the code is transferred to control unit by a conventional RS232C serial communication. The GPS receiver is normally in a standby mode, and automatically activated to inform the caretakers of his/her current location when a patient is in a critical condition.

Figure 21:
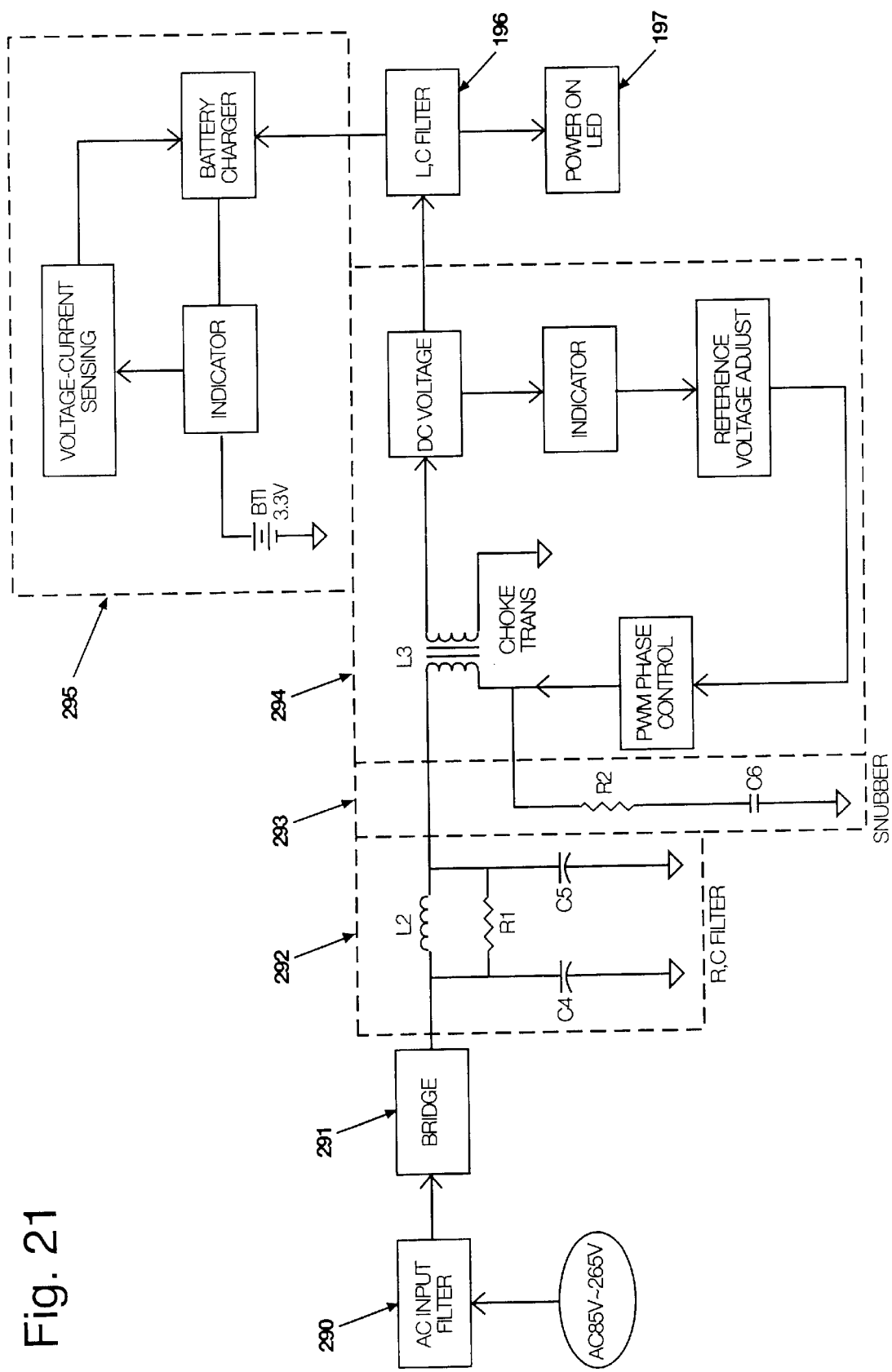
FIG. 21 depicts a switch mode power supply (SMPS) and charger.
Figure 22:
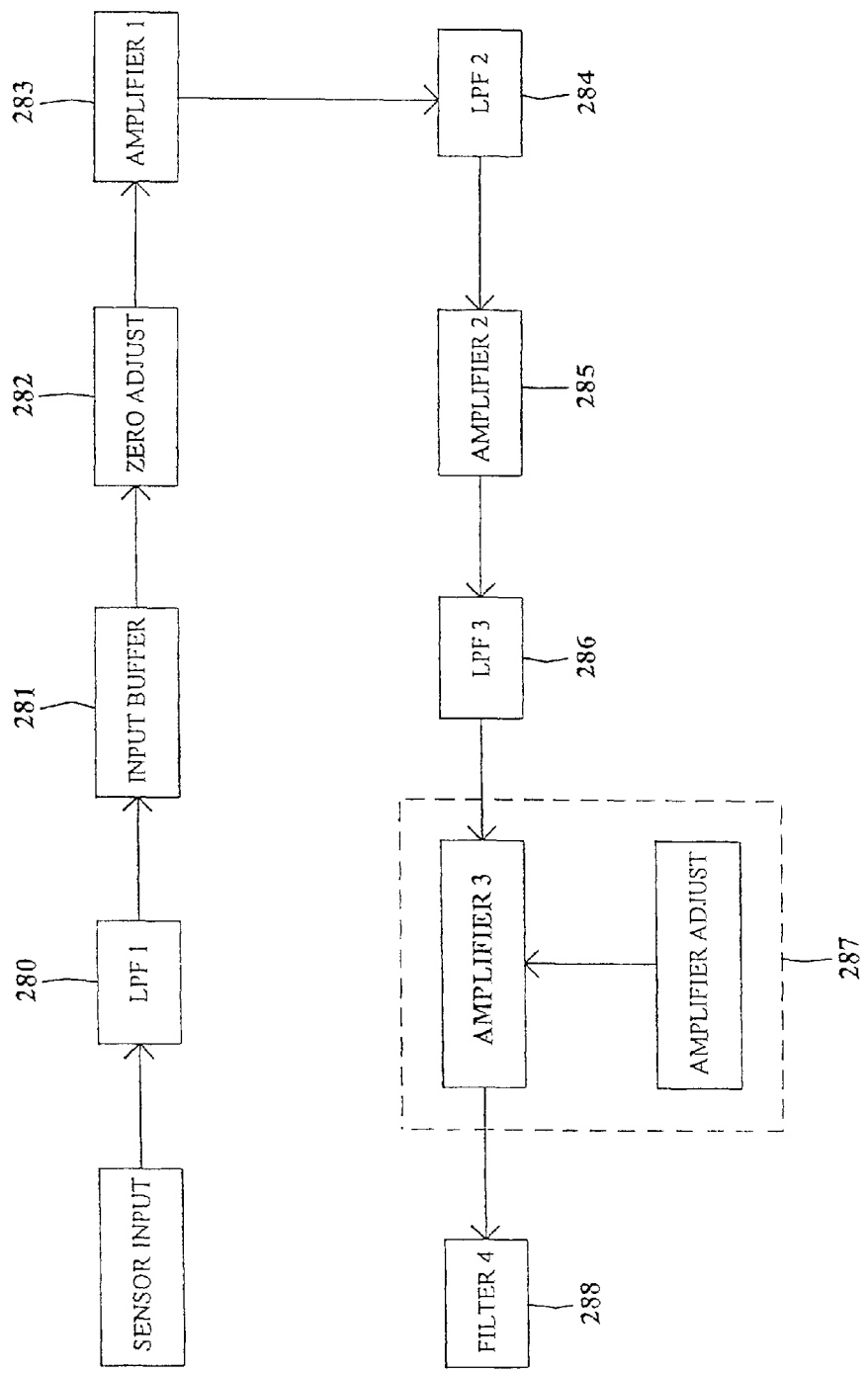
FIGS. 22 and 23 are block diagrams of a signal conditioner for the alarm system of FIG. 16, and the micro-control unit for the alarm system of FIG. 16, respectively.
Figure 23:
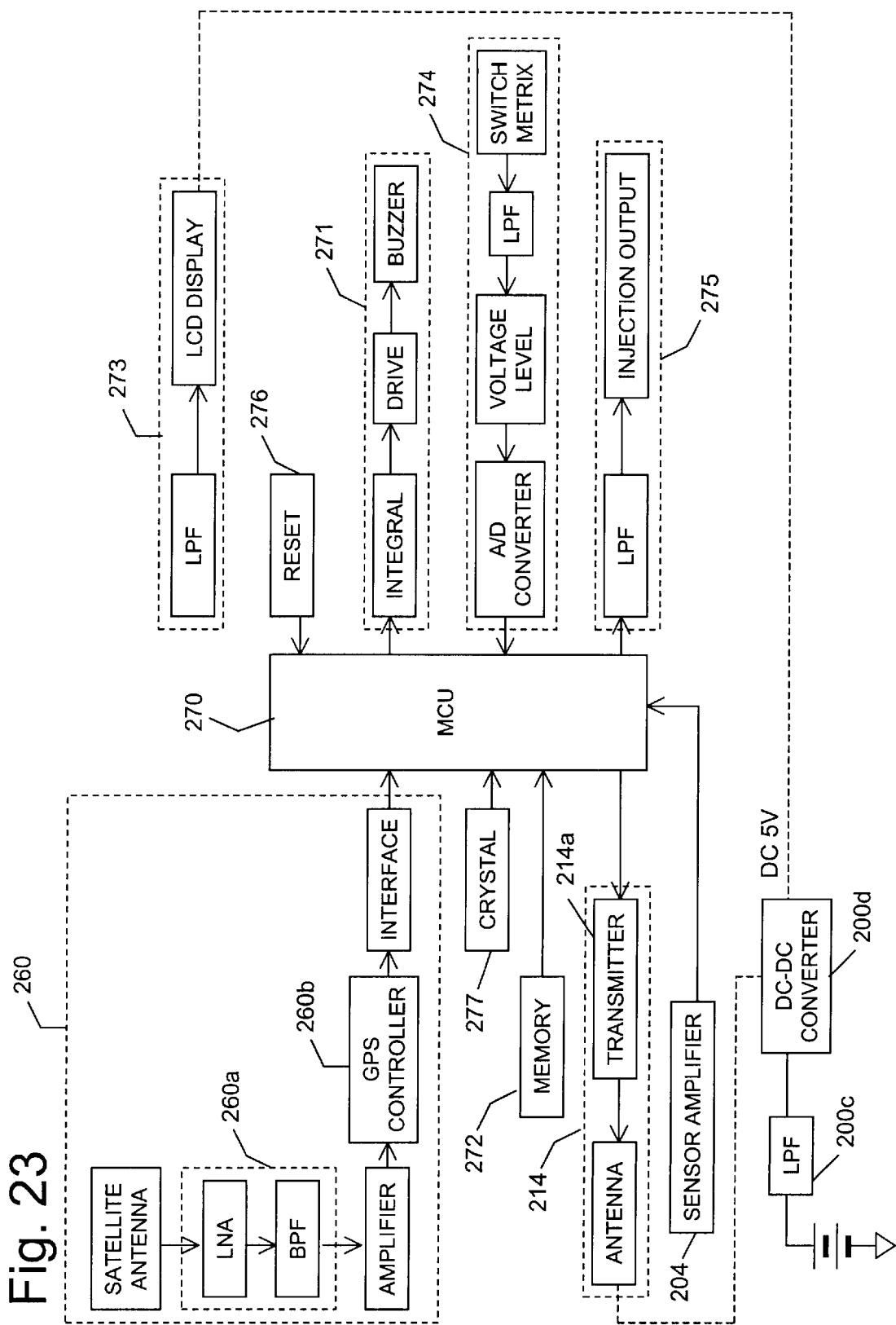

FIGS. 21, 22 and 23 are block diagrams of three major components of the automatic alarm system for a prototype device. FIG. 21 shows a switch mode power supply (SMPS) and charger; FIG. 22 shows a signal conditioning circuit, and FIG. 23 depicts the overall control unit.

As seen in FIG. 21 which is a block diagram of a free voltage input S.M.P.S. circuit and charger block, AC power noise is filtered in an AC input filter 290 before bridge circuit 291 in which AC power (AC 85V to 265V) is converted to all wave. RC filter circuit 292 converts the all wave into DC power at the same time DC power noise is filtered. Nevertheless, the converted DC power has spark noise and can be preferably removed by using of snubber circuit 293.

The level of converted DC voltage can be preferably adjusted in a adjustment circuit 294 between 4.5V and 5V, which is usually a little higher than the voltage capacity of battery to be charged. The converted DC power voltage is preferably filtered by LC filter 296 to reduce the noise generated during the adjustment of DC voltage level. The battery charging circuit 295 controls the charging current and voltage, depending on how much the rechargeable battery is being charged.

A block diagram of the signal conditioner is presented in FIG. 22. The signal level from a sensor is very low and vulnerable to environmental noise. Before amplification the low level signal is preferably filtered by a RC filter, low pass filter 1 (LPF1), 280. Otherwise, both signal and noise are amplified and the signal cannot be distinguished from the noise.

The filtered signal is preferably amplified with a gain of approximately 10. The higher amplification gain for the low levels of signal possibly deteriorates the signal and is unable to restore the signal from the noise. The amplified signal is filtered by conventional RC filter (LPF2) 284 to reduce noises again.

As the secondary amplification in amplifier2 285, an approximate gain of 100 is preferably engaged to give an enough dynamic range of the A/D converter in the control unit, and the noise filter, LPF3 286 is also used for reducing noises.

Although the total amplification gain of the previous amplifiers should be 1000, multiplied by 100, the total gain of 1000 cannot be achieved in a practical sense. The reason is that the devices such op-amps, resistors, and capacitors have their own errors. In order to compensate this discrepancy in gain, a variable resistor should be preferably adjusted in the amplifier adjustment circuit 287. The total amplification gain can be adjusted by an initial input signal from a sensor. Desirably, a surge filter 288 is included to prevent damage from voltage surges.

As shown in the block diagram of FIG. 23, a microprocessor control unit (MCU) 270 preferably controls all devices of a GPS receiver 260, a wireless communication device 214, a signal conditioner 204, a buzzer and recorded voice 271, a memory 272, a display 273, a key in 274, an auto injection device 275 and a reset 276. It operates under the designated speed, which can be determined by a crystal 277. MCU 270 can access to memory for storing and retrieving data, which are needed to operate the automatic alarm system. The user can initialize MCU 270 by engaging reset switch 276. Reset 276 will make MCU 270 along with the whole system return to the initial condition, as if the system is turned off and turned on again. The MCU can preferably display information in the automatic alarm system on the LCD (Liquid Clear Display) 273. Users can command MCU 270 by the pre assigned key inputs 274, which are preferably detected by voltage level.

The signals bearing location code from GPS satellites 261 are preferably firsthand filtered by BPF (Band Path Filter) 260a with the 20 MHz of bandwidth and 1575.42 MHz of center frequency, which is a nominal frequency band of GPS. Since the signals from the satellites 261 are received as a form of coded data, they should be decoded in GPS controller module 260b. The decoded coordinate data of X/Y/Z directions are then transferred to MCU 270 by RS232C serial communication.

The analog signal from signal conditioner 204 is converted to digital signal by MCU 270, which has the A/D converter inside. The digital signal is utilized for comparing pre-determined threshold to monitor patient's condition.

The output signal of MCU 270 to activate alarming buzzer 271 preferably passes a current drive 271a to control sound level. Along with alarming sound, when critical condition is detected, MCU 271 provides an activated signal to an automatic injection device 275 in concern.

On alarm, the recorded and input information as well as location coordinates of patient are transmitted to a pre-determined destination by using a communication device 214. A wireless communication device 214 is preferably used for an automatic alarm informing system.

While the health alarm system of the invention is herein described primarily in terms of a hydrogel biosensor in which changes in osmotic pressure reflect changes in a blood analyte level, the health alarm system may instead use an entirely different type of biosensor, for example one which detects cardiac rhythm, blood coagulation factors, or any other desired health determinant, or which uses a method other than measurement of osmotic pressure to determine the blood analyte level, or measures a blood analyte unrelated to diabetes. The delivery of an alarm to concerned individuals not on the same premises as the patient, and the further potential offered by including a GPS unit to provide patient location data to those concerned individuals in the event of an emergency, are potentially of benefit to patients suffering from diverse conditions who nevertheless wish to travel, hike, fish, etc.

Those skilled in the art will appreciate that the combination of a biosensor with an automated telephonic notification system provides significant advantages for improving health care. Not only is the patient warned of a condition which can cause physiologic damage, but also health care workers are notified if the situation surpasses a predetermined threshold. Thus, for example, if the diabetic has gone into a hypoglycemic shock, medical personnel (or relatives of the patient) can respond and provide appropriate medical care. Such a system is particularly advantageous for those who live alone and those of limited mobility. The embodiment including a GPS unit (FIG. 16) is particularly valuable for travelers, as the caretakers to whom the alarm is sent will also receive information about the patient's location.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A biosensor for measuring the concentration of molecules of an analyte in a body fluid, comprising:
   a polymeric hydrogel having pendant moieties that are charged under physiological conditions;
   an analyte binding molecule immobilized in the hydrogel and capable of binding the free analyte;
   analyte molecules immobilized in the hydrogel; and
   pressure detection means for measuring the osmotic pressure of the hydrogel.

2. The biosensor of claim 1, wherein the hydrogel is disposed within a rigid enclosure with at least one area permeable to contact between the hydrogel and a fluid being tested and permitting free analyte molecules to diffuse into the hydrogel from the fluid.

3. The biosensor of claim 1, wherein the pressure detection means comprises a diaphragm disposed within the enclosure in contact with the hydrogel, and a pressure transducer operably engaged with the diaphragm to measure pressure on the diaphragm.

4. The biosensor of claim 1, further including reporting means operably associated with the pressure-detection means for reporting a data signal reflective of the pressure changes in the hydrogel.

5. The biosensor of claim 2, wherein the permeable area is an open end in the rigid enclosure, and said open end is sealed by a semipermeable membrane that allows the free analyte molecules to diffuse into the hydrogel.

6. The biosensor of claim 4, wherein the enclosure is conjugated with heparin and polyethylene glycol.

7. The biosensor of claim 4 wherein the enclosure is coated with a semipermeable membrane and a biodegradable polymer on the semipermeable membrane.

8. The biosensor of claim 1 wherein the analyte binding molecule is selected from the group consisting of: antibodies, enzymes, membrane receptors, kinases, Protein A, Poly U, Poly A, Poly lysine, triazine dye, nucleoside, boronic acid, thiol, heparin, polysaccharides, Coomassie blue, azure A, and metal-binding peptides, proteins, and chelating agents.

9. The biosensor of claim 1 wherein the immobilized analyte is selected from the group consisting of: antigens, enzyme cofactors, enzyme substrates, enzyme inhibitors, IGG, sugar, carbohydrate, nucleic acids, nucleotide, nucleoside, cysteine, arginine, lysine, protamine, heparin, dyes, and metal ions.

10. The biosensor of claim 1, wherein the charged pendant groups are present at a density chosen to optimize the amount of hydrogel swelling in response to changes in level of free analyte molecules.

11. The biosensor of claim 1, wherein the immobilized analyte molecules and immobilized analyte binding molecule are present at respective densities chosen to optimize the amount of hydrogel swelling in response to changes in level of free analyte molecules.

12. The biosensor of claim 3 wherein the pressure transducer is selected from the group consisting of a piezoelectric transducer, a piezoresistive transducer, and a capacitive transducer.

13. The biosensor of claim 4, further including computing means connected to receive the data signal from the reporting means, said computing means being constructed to compare the data signal to a calibration curve to compute a concentration of the free analyte in the body fluids and produce an output signal representing the free analyte concentration.

14. The biosensor of claim 4, wherein the reporting means is a battery powered telemeter, and further including receiving means positioned at a location remote to the patient for receiving the data signal.

15. The biosensor of claim 14, further including computing means operably associated with the receiving means for comparing the data signal to a calibration curve to compute a concentration of the free analyte in the body fluids and produce an output signal representing the analyte concentration.

16. The biosensor of claim 14, wherein the computer means is further configured to compare the detected analyte concentration to a predetermined safe range, and to produce an alarm signal when the detected analyte concentration falls outside the safe range.

17. A method of determining the concentration of free analyte in a solution, comprising the steps of:
    providing a hydrogel having pendant charged moieties, analyte molecules, and analyte-specific binding molecules covalently immobilized therein;
    enclosing the hydrogel in a rigid structure which has at least one permeable portion available for contacting a test fluid with the hydrogel, the permeable portion constructed to permit free analyte to diffuse into the hydrogel;
    contacting the hydrogel sequentially with a series of calibration solutions having known concentrations of free analyte;
    measuring osmotic pressure in the hydrogel for each of the calibration solutions to produce a calibration curve of osmotic pressure versus analyte concentration;
    contacting the hydrogel with the test fluid, and measuring a resulting osmotic pressure; and
    comparing the resulting osmotic pressure with the calibration curve to determine analyte concentration of the test fluid.

18. The method of claim 17, wherein said steps of measuring the osmotic pressure are accomplished by disposing pressure sensing means within the rigid structure and in contact with the hydrogel for measuring osmotic pressure of the hydrogel and producing a data signal reflective thereof.

19. The method of claim 18, wherein said pressure sensing means comprises a diaphragm disposed within the rigid enclosure in contact with the hydrogel, and a pressure transducer operably engaged with the diaphragm to measure pressure on the diaphragm.

20. A sensor for measuring the concentration of free molecules of an analyte in a fluid, comprising:
    a rigid enclosure having an open end and a closed end, the open end being covered by a semipermeable membrane;
    a diaphragm positioned within the enclosure between the semipermeable membrane and the closed end;
    a polymeric hydrogel having pendant moieties which are charged at physiological pH, the hydrogel being enclosed between the semipermeable membrane and the diaphragm such that changes in osmotic pressure within the hydrogel are accompanied by changes in pressure exerted on the diaphragm;
    analyte binding molecules immobilized within the hydrogel;
    analyte molecules immobilized within the hydrogel; and
    a pressure transducer operatively engaged to the diaphragm.

21. The sensor of claim 20, further including a battery powered telemeter operatively engaged to the transducer.

22. A method for using a biosensor to measure the concentration of free molecules of an analyte in a fluid, including:
    a first step of providing a biosensor comprising:
        a rigid, biocompatible enclosure having an open end and a closed end, the open end being covered by a semipermeable membrane;
        a diaphragm positioned between the semipermeable membrane and the closed end such that changes in osmotic pressure within the hydrogel are accompanied by changes in pressure exerted on the diaphragm;
        a polymeric hydrogel having pendant moieties which are charged at physiological pH, the hydrogel being enclosed between the semipermeable membrane and the diaphragm such that changes in osmotic pressure within the hydrogel are accompanied by changes in pressure exerted on the diaphragm;
        analyte binding molecules immobilized within the hydrogel;
        analyte immobilized within the hydrogel, and
        osmotic pressure sensing means operatively engaged to the diaphragm for sensing the osmotic pressure exerted thereon and providing a data signal reflective thereof;
    a second step of providing computing means connected to receive the data signal, compare it to a predetermined calibration curve of osmotic pressure vs, concentration of free analyte molecules, and output a concentration value;
    a third step of inserting the biosensor into the fluid and allowing sufficient time for free analyte molecules to diffuse to equilibrium within the hydrogel; and
    a fourth step of reading the concentration value output by the computing means.

23. The biosensor of claim 1, wherein the pressure detection means for measuring the osmotic pressure of the hydrogel reports a data signal reflective of the pressure of the hydrogel, and additionally including means for generating an alarm signal responsive to the reported data signal if outside a predetermined range, and a transmitter for transmitting the alarm signal to a remote location.

24. The biosensor of claim 23, additionally including a receiver for receiving alarm signals from the transmitter, and a dialer for dialing a telephone in response to an alarm signal received from the transmitter.

25. The biosensor of claim 23, additionally including an injection device for injecting agents into a person in response to alarm signals from the means for generating an alarm signal.

26. The biosensor of claim 23, additionally including an injection device for injecting agents into a person in response to reported data signal.

27. The biosensor of claim 23, additionally including a GPS unit operably associated with the transmitter for transmitting a location signal reflective of a patient's location in addition to the alarm signal.

* * * * *